United States Patent
Wright et al.

(10) Patent No.: US 11,354,818 B2
(45) Date of Patent: Jun. 7, 2022

(54) MEDICAL IMAGING SYSTEM, METHOD AND COMPUTER PROGRAM PRODUCT

(71) Applicant: Sony Corporation, Tokyo (JP)

(72) Inventors: Christopher Wright, London (GB); Matthew Lawrenson, Lausanne (CH); Taro Azuma, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 10 days.

(21) Appl. No.: 16/613,814

(22) PCT Filed: May 28, 2018

(86) PCT No.: PCT/JP2018/020388
§ 371 (c)(1),
(2) Date: Nov. 15, 2019

(87) PCT Pub. No.: WO2018/235533
PCT Pub. Date: Dec. 27, 2018

(65) Prior Publication Data
US 2020/0175719 A1 Jun. 4, 2020

(30) Foreign Application Priority Data
Jun. 21, 2017 (EP) .................................... 17177212

(51) Int. Cl.
*G06K 9/00* (2022.01)
*G06T 7/73* (2017.01)
(Continued)

(52) U.S. Cl.
CPC ................ *G06T 7/74* (2017.01); *A61B 90/37* (2016.02); *G06T 5/20* (2013.01); *G06T 5/50* (2013.01);
(Continued)

(58) Field of Classification Search
CPC ............ A61B 1/3132; A61B 2090/363; A61B 2090/364; A61B 90/37; G06T 2207/10016; G06T 2207/10024; G06T 2207/10056; G06T 2207/10068; G06T 2207/30076; G06T 2207/30101; G06T 5/10; G06T 5/20; G06T 5/50; G06T 7/248; G06T 7/262;
(Continued)

(56) References Cited

U.S. PATENT DOCUMENTS

2013/0304446 A1* 11/2013 Rabinovitz ........... G06T 7/0012
703/11
2016/0166336 A1* 6/2016 Razzaque .............. A61B 34/25
606/130

(Continued)

OTHER PUBLICATIONS

Hao-yu Wu, Eulerian Video Magnification for Revealing Subtle Changes in the World, Jul. 2012, ACM Transactions on Graphics, vol. 31, No. 4, Article 65.*

(Continued)

*Primary Examiner* — Xin Jia
(74) *Attorney, Agent, or Firm* — Xsensus LLP

(57) ABSTRACT

A surgical imaging system comprising circuitry configured to accentuate an image characteristic of an area in captured images; identify the change of the image characteristic in the area; and identify the position of a physiological feature relative to the surgical device on the basis of the change in the image characteristic.

21 Claims, 13 Drawing Sheets

(51) Int. Cl.
| | |
|---|---|
| *A61B 90/00* | (2016.01) |
| *G06T 7/50* | (2017.01) |
| *G06T 7/90* | (2017.01) |
| *G06T 7/246* | (2017.01) |
| *G06T 5/20* | (2006.01) |
| *G06T 5/50* | (2006.01) |
| *A61B 1/313* | (2006.01) |

(52) U.S. Cl.
CPC ............... *G06T 7/248* (2017.01); *G06T 7/50* (2017.01); *G06T 7/90* (2017.01); *A61B 1/3132* (2013.01); *A61B 2090/363* (2016.02); *A61B 2090/364* (2016.02); *G06T 2207/10016* (2013.01); *G06T 2207/10024* (2013.01); *G06T 2207/10056* (2013.01); *G06T 2207/10068* (2013.01); *G06T 2207/30101* (2013.01)

(58) Field of Classification Search
CPC .. G06T 7/50; G06T 7/579; G06T 7/74; G06T 7/90; G16H 30/40; H04N 5/232; H04N 9/045; H04N 9/64
See application file for complete search history.

(56) References Cited

U.S. PATENT DOCUMENTS

| | | | |
|---|---|---|---|
| 2017/0000392 A1 | 1/2017 | Smith | |
| 2017/0209118 A1* | 7/2017 | Yang | ................... A61B 8/4254 |
| 2018/0116731 A1* | 5/2018 | State | ...................... A61B 34/20 |

OTHER PUBLICATIONS

International Search Report and Written Opinion dated Nov. 14, 2018 for PCT/JP2018/020388 filed on May 28, 2018, 17 pages.
Wu et al., "Eulerian Video Magnification for Revealing Subtle Changes in the World", ACM Transactions on Graphics, vol. 31, No. 4, Article 65, Jul. 2012, pp. 1-8.
Adams et al., "Algorithm-Based Motion Magnification for Video Processing in Urological Laparoscopy", Journal of Endourology,Laparoscopy and Robotic Surgery, vol. 31, No. 6, Jun. 2017, pp. 583-587.
Office Action issued in Japanese Application PCT/JP2018/020388 dated Nov. 12, 2019.
Wadhwa, N., et al., "Phase-Based Video Motion Processing", ACM Transactions on Graphics, vol. 32, No. 4, 10 Pages total, (Jul. 2013).

* cited by examiner

Figure 2
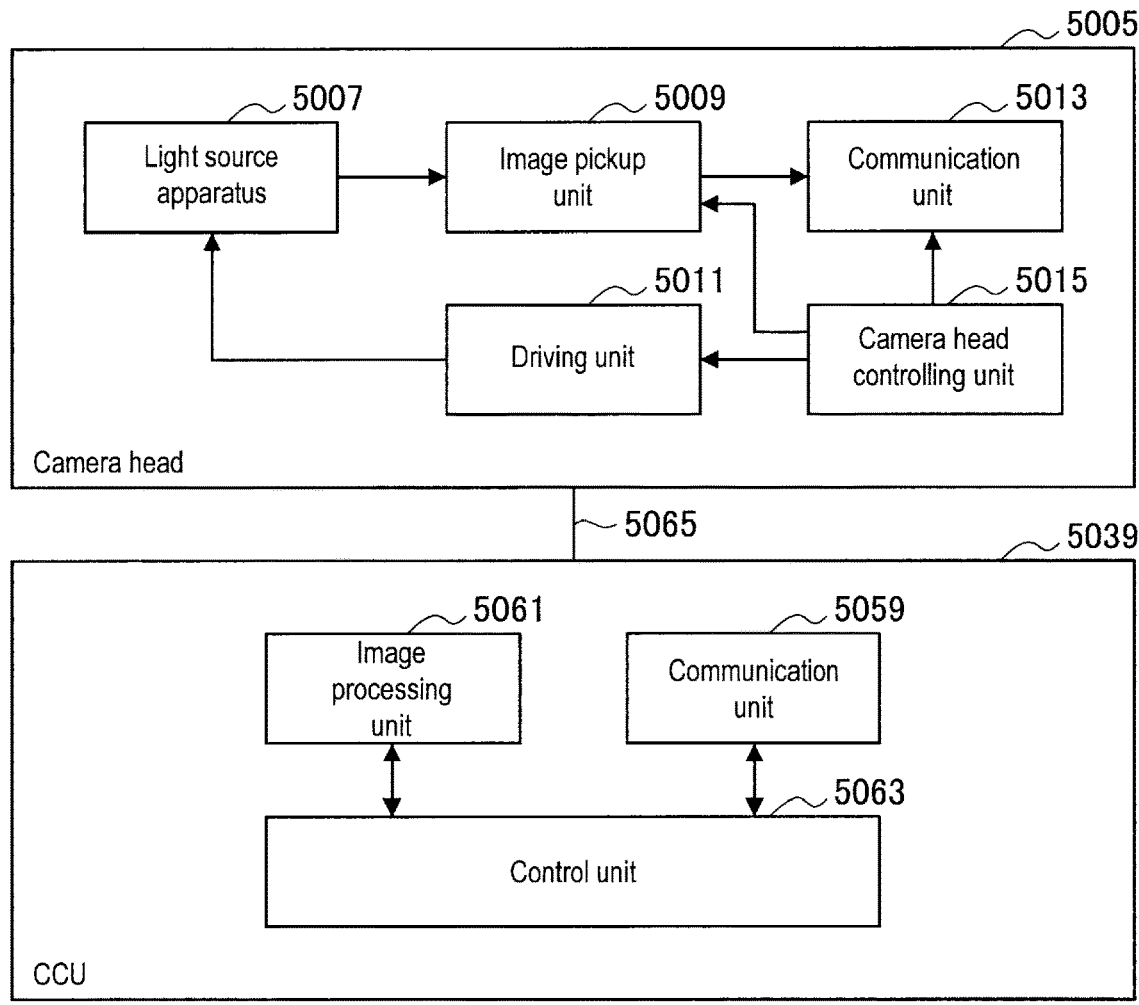
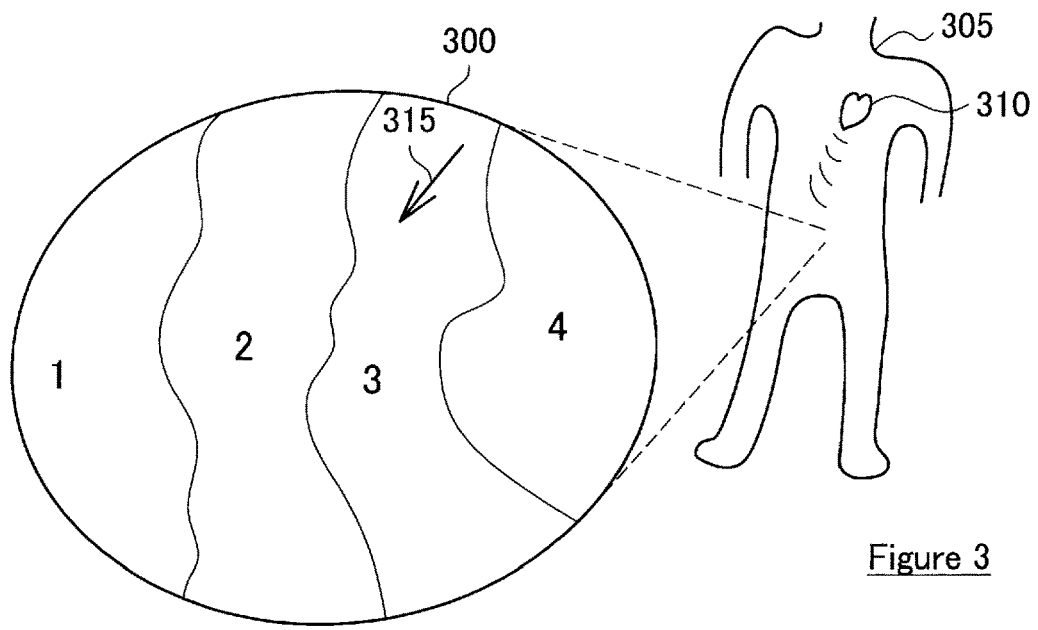
Figure 3

Branch 1:Normal pressure
Branch 2:Minimal pressure
Branch 3:Partially reduced pressure

MEDICAL IMAGING SYSTEM, METHOD AND COMPUTER PROGRAM PRODUCT

CROSS REFERENCE TO RELATED APPLICATIONS

This application is based on PCT filing PCT/JP2018/020388, filed on May 28, 2018, which claims the benefit of EP17177212.2, filed Jun. 21, 2017, the entire contents of each are incorporated herein by reference.

TECHNICAL FIELD

The present disclosure relates to a surgical imaging system and method.

BACKGROUND ART

The "background" description provided herein is for the purpose of generally presenting the context of the disclosure. Work of the presently named inventors, to the extent it is described in the background section, as well as aspects of the description which may not otherwise qualify as prior art at the time of filing, are neither expressly or impliedly admitted as prior art against the present disclosure.

A problem when performing surgical procedures such as endoscopy or microscopy on internal anatomies such as the colon is that they have few landmarks and can vary considerably between patients and over the course of surgery. This makes it difficult to assess and interpret images and videos of internal anatomies.

In addition, the lack of landmarks makes it difficult to locate and re-locate specific areas within a patient. It is known to tattoo and apply suction cups to areas to assist in relocating an area. However, as internal organs move and are non-rigid, these techniques can be unreliable. This leads to increased procedure times and complications from the increased risk of so-called "wrong site" procedures.

It is an aim of the present disclosure to address at least these issues.

CITATION LIST

Non Patent Literature

[NPL 1] Phase-based Video Motion Processing, Neal Wadhwa, Michael Rubinstein, Fredo Durand, William t. Freeman. ACM Transactions on Graphics, Vol. 32, Number 4 (Proc SIGGRAPH), 2013.

SUMMARY

According to one aspect, there is provided a surgical imaging system comprising circuitry configured to accentuate an image characteristic of an area in captured images; identify the change of the image characteristic in the area; and identify the position of a physiological feature relative to the surgical device on the basis of the change in the image characteristic.

According to another aspect, there is provided a surgical imaging system comprising circuitry configured to: accentuate the colour and/or motion of an area in captured images; compare the accentuated motion to a stored accentuated motion and identify the material of the object based upon the comparison.

According to another aspect, there is provided a surgical imaging system comprising circuitry configured to: accentuate the colour and/or motion of an area in captured images; compare the accentuated motion to a stored accentuated motion and identify a landmark based on the comparison.

According to another aspect, there is provided a surgical imaging system comprising circuitry configured to: accentuate the colour and/or motion of an area in captured images; and identify a landmark based on a characteristic feature in the accentuated motion.

According to another aspect, there is provided a surgical imaging system comprising circuitry configured to: identify a captured image of a pattern of vasculature as a landmark; store the captured pattern; compare subsequent captured images to the stored pattern and identify the subsequent image as the landmark on the basis of the comparison The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF DRAWINGS

A more complete appreciation of the disclosure and many of the attendant advantages thereof will be readily obtained as the same becomes better understood by reference to the following detailed description when considered in connection with the accompanying drawings.

FIG. 2 is a block diagram depicting an example of a functional configuration of a camera head and a camera control unit (CCU) depicted in FIG. 1.

FIGS. 3 and 4 schematically show an endoscope view explaining embodiments of the disclosure.

DESCRIPTION OF EMBODIMENTS

Figure 1:
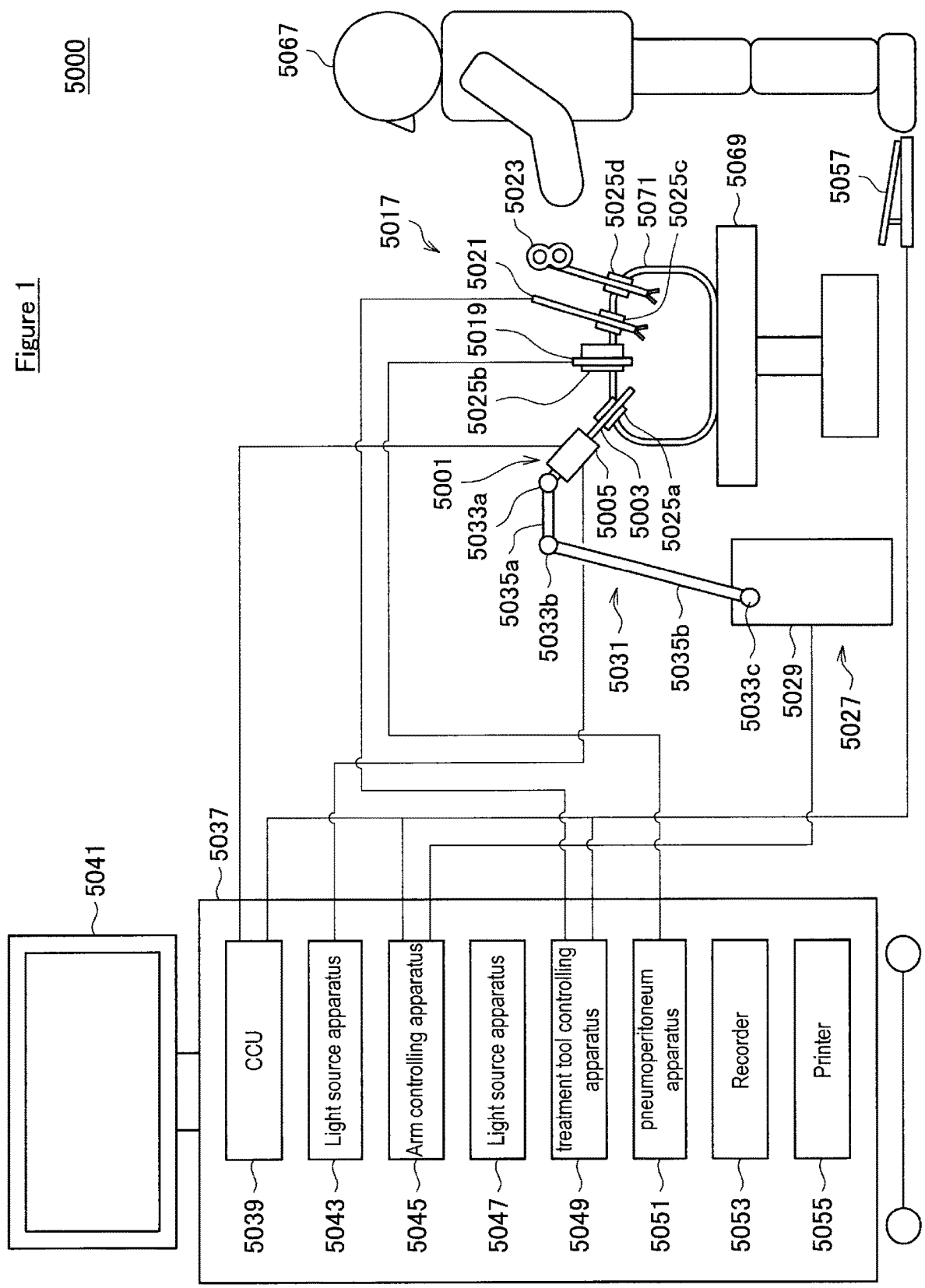
FIG. 1 is a view depicting an example of a schematic configuration of an endoscopic surgery system.

Referring now to the drawings, wherein like reference numerals designate identical or corresponding parts throughout the several views.

1. Application

<<1. Application>>

The technology according to an embodiment of the present disclosure can be applied to various products. For example, the technology according to an embodiment of the present disclosure may be applied to an endoscopic surgery system.

FIG. 1 is a view depicting an example of a schematic configuration of an endoscopic surgery system 5000 to which the technology according to an embodiment of the present disclosure can be applied. In FIG. 1, a state is illustrated in which a surgeon (medical doctor) 5067 is using the endoscopic surgery system 5000 to perform surgery for a patient 5071 on a patient bed 5069. As depicted, the endoscopic surgery system 5000 includes an endoscope 5001, other surgical tools 5017, a supporting arm apparatus 5027 which supports the endoscope 5001 thereon, and a cart 5037 on which various apparatus for endoscopic surgery are mounted.

In endoscopic surgery, in place of incision of the abdominal wall to perform laparotomy, a plurality of tubular aperture devices called trocars 5025a to 5025d are used to puncture the abdominal wall. Then, a lens barrel 5003 of the endoscope 5001 and the other surgical tools 5017 are inserted into body lumens of the patient 5071 through the trocars 5025a to 5025d. In the example depicted, as the other surgical tools 5017, a pneumoperitoneum tube 5019, an energy treatment tool 5021 and forceps 5023 are inserted into body lumens of the patient 5071. Further, the energy treatment tool 5021 is a treatment tool for performing incision and peeling of a tissue, sealing of a blood vessel or the like by high frequency current or ultrasonic vibration. However, the surgical tools 5017 depicted are mere examples at all, and as the surgical tools 5017, various surgical tools which are generally used in endoscopic surgery such as, for example, a pair of tweezers or a retractor may be used.

An image of a surgical region in a body lumen of the patient 5071 imaged by the endoscope 5001 is displayed on a display apparatus 5041. The surgeon 5067 would use the energy treatment tool 5021 or the forceps 5023 while watching the image of the surgical region displayed on the display apparatus 5041 on the real time basis to perform such treatment as, for example, resection of an affected area. It is to be noted that, though not depicted, the pneumoperitoneum tube 5019, the energy treatment tool 5021 and the forceps 5023 are supported by the surgeon 5067, an assistant or the like during surgery.

(Supporting Arm Apparatus)

The supporting arm apparatus 5027 includes an arm unit 5031 extending from a base unit 5029. In the example depicted, the arm unit 5031 includes joint portions 5033a, 5033b and 5033c and links 5035a and 5035b and is driven under the control of an arm controlling apparatus 5045. The endoscope 5001 is supported by the arm unit 5031 such that the position and the posture of the endoscope 5001 are controlled. Consequently, stable fixation in position of the endoscope 5001 can be implemented.

(Endoscope)

The endoscope 5001 includes the lens barrel 5003 which has a region of a predetermined length from a distal end thereof to be inserted into a body lumen of the patient 5071, and a camera head 5005 connected to a proximal end of the lens barrel 5003. In the example depicted, the endoscope 5001 is depicted which includes as a hard mirror having the lens barrel 5003 of the hard type. However, the endoscope 5001 may otherwise be configured as a soft mirror having the lens barrel 5003 of the soft type.

The lens barrel 5003 has, at a distal end thereof, an opening in which an objective lens is fitted. A light source apparatus 5043 is connected to the endoscope 5001 such that light generated by the light source apparatus 5043 is introduced to a distal end of the lens barrel by a light guide extending in the inside of the lens barrel 5003 and is irradiated toward an observation target in a body lumen of the patient 5071 through the objective lens. It is to be noted that the endoscope 5001 may be a direct view mirror or may be a perspective view mirror or a side view mirror.

An optical system and an image pickup element are provided in the inside of the camera head 5005 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 5039. It is to be noted that the camera head 5005 has a function incorporated therein for suitably driving the optical system of the camera head 5005 to adjust the magnification and the focal distance.

It is to be noted that, in order to establish compatibility with, for example, a stereoscopic vision (three dimensional (3D) display), a plurality of image pickup elements may be provided on the camera head 5005. In this case, a plurality of relay optical systems are provided in the inside of the lens barrel 5003 in order to guide observation light to each of the plurality of image pickup elements.

(Various Apparatus Incorporated in Cart)

The CCU 5039 includes a central processing unit (CPU), a graphics processing unit (GPU) or the like and integrally controls operation of the endoscope 5001 and the display apparatus 5041. In particular, the CCU 5039 performs, for an image signal received from the camera head 5005, various image processes for displaying an image based on the image signal such as, for example, a development process (demosaic process). The CCU 5039 provides the image signal for which the image processes have been performed to the display apparatus 5041. Further, the CCU 5039 transmits a control signal to the camera head 5005 to control driving of the camera head 5005. The control signal may include information relating to an image pickup condition such as a magnification or a focal distance.

The display apparatus 5041 displays an image based on an image signal for which the image processes have been performed by the CCU 5039 under the control of the CCU 5039. If the endoscope 5001 is ready for imaging of a high resolution such as 4K (horizontal pixel number 3840× vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus 5041. Where the apparatus is ready for imaging of a high resolution such as 4K or 8K, if the display apparatus used as the display apparatus 5041 has a size of equal to or not less than 55 inches, then a more immersive experience can be obtained. Further, a plurality of display apparatus 5041 having different resolutions and/or different sizes may be provided in accordance with purposes.

The light source apparatus 5043 includes a light source such as, for example, a light emitting diode (LED) and supplies irradiation light for imaging of a surgical region to the endoscope 5001.

The arm controlling apparatus 5045 includes a processor such as, for example, a CPU and operates in accordance with a predetermined program to control driving of the arm unit 5031 of the supporting arm apparatus 5027 in accordance with a predetermined controlling method.

An inputting apparatus 5047 is an input interface for the endoscopic surgery system 5000. A user can perform inputting of various kinds of information or instruction inputting to the endoscopic surgery system 5000 through the inputting apparatus 5047. For example, the user would input various kinds of information relating to surgery such as physical information of a patient, information regarding a surgical procedure of the surgery and so forth through the inputting apparatus 5047. Further, the user would input, for example, an instruction to drive the arm unit 5031, an instruction to change an image pickup condition (type of irradiation light, magnification, focal distance or the like) by the endoscope 5001, an instruction to drive the energy treatment tool 5021 or the like through the inputting apparatus 5047.

The type of the inputting apparatus 5047 is not limited and may be that of any one of various known inputting apparatus. As the inputting apparatus 5047, for example, a mouse, a keyboard, a touch panel, a switch, a foot switch 5057 and/or a lever or the like may be applied. Where a touch panel is used as the inputting apparatus 5047, it may be provided on the display face of the display apparatus 5041.

Otherwise, the inputting apparatus 5047 is a device to be mounted on a user such as, for example, a glasses type wearable device or a head mounted display (HMD), and various kinds of inputting are performed in response to a gesture or a line of sight of the user detected by any of the devices mentioned. Further, the inputting apparatus 5047 includes a camera which can detect a motion of a user, and various kinds of inputting are performed in response to a gesture or a line of sight of a user detected from a video imaged by the camera. Further, the inputting apparatus 5047 includes a microphone which can collect the voice of a user, and various kinds of inputting are performed by voice collected by the microphone. By configuring the inputting apparatus 5047 such that various kinds of information can be inputted in a contactless fashion in this manner, especially a user who belongs to a clean area (for example, the surgeon 5067) can operate an apparatus belonging to an unclean area in a contactless fashion. Further, since the user can operate an apparatus without releasing a possessed surgical tool from its hand, the convenience to the user is improved.

A treatment tool controlling apparatus 5049 controls driving of the energy treatment tool 5021 for cautery or incision of a tissue, sealing of a blood vessel or the like. A pneumoperitoneum apparatus 5051 feeds gas into a body lumen of the patient 5071 through the pneumoperitoneum tube 5019 to inflate the body lumen in order to secure the field of view of the endoscope 5001 and secure the working space for the surgeon. A recorder 5053 is an apparatus capable of recording various kinds of information relating to surgery. A printer 5055 is an apparatus capable of printing various kinds of information relating to surgery in various forms such as a text, an image or a graph.

In the following, especially a characteristic configuration of the endoscopic surgery system 5000 is described in more detail.

(Supporting Arm Apparatus)

The supporting arm apparatus 5027 includes the base unit 5029 serving as a base, and the arm unit 5031 extending from the base unit 5029. In the example depicted, the arm unit 5031 includes the plurality of joint portions 5033a, 5033b and 5033c and the plurality of links 5035a and 5035b connected to each other by the joint portion 5033b. In FIG. 1, for simplified illustration, the configuration of the arm unit 5031 is depicted in a simplified form. Actually, the shape, number and arrangement of the joint portions 5033a to 5033c and the links 5035a and 5035b and the direction and so forth of axes of rotation of the joint portions 5033a to 5033c can be set suitably such that the arm unit 5031 has a desired degree of freedom. For example, the arm unit 5031 may preferably be configured such that it has a degree of freedom equal to or not less than 6 degrees of freedom. This makes it possible to move the endoscope 5001 freely within the movable range of the arm unit 5031. Consequently, it becomes possible to insert the lens barrel 5003 of the endoscope 5001 from a desired direction into a body lumen of the patient 5071.

An actuator is provided in each of the joint portions 5033a to 5033c, and the joint portions 5033a to 5033c are configured such that they are rotatable around predetermined axes of rotation thereof by driving of the respective actuators. The driving of the actuators is controlled by the arm controlling apparatus 5045 to control the rotational angle of each of the joint portions 5033a to 5033c thereby to control driving of the arm unit 5031. Consequently, control of the position and the posture of the endoscope 5001 can be implemented. Thereupon, the arm controlling apparatus 5045 can control driving of the arm unit 5031 by various known controlling methods such as force control or position control.

For example, if the surgeon 5067 suitably performs operation inputting through the inputting apparatus 5047 (including the foot switch 5057), then driving of the arm unit 5031 may be controlled suitably by the arm controlling apparatus 5045 in response to the operation input to control the position and the posture of the endoscope 5001. After the endoscope 5001 at the distal end of the arm unit 5031 is moved from an arbitrary position to a different arbitrary position by the control just described, the endoscope 5001 can be supported fixedly at the position after the movement. It is to be noted that the arm unit 5031 may be operated in a master-slave fashion. In this case, the arm unit 5031 may be remotely controlled by the user through the inputting apparatus 5047 which is placed at a place remote from the surgery room.

Further, where force control is applied, the arm controlling apparatus 5045 may perform power-assisted control to drive the actuators of the joint portions 5033a to 5033c such that the arm unit 5031 may receive external force by the user and move smoothly following the external force. This makes it possible to move, when the user directly touches with and moves the arm unit 5031, the arm unit 5031 with comparatively weak force. Accordingly, it becomes possible for the user to move the endoscope 5001 more intuitively by a simpler and easier operation, and the convenience to the user can be improved.

Here, generally in endoscopic surgery, the endoscope 5001 is supported by a medical doctor called scopist. In contrast, where the supporting arm apparatus 5027 is used, the position of the endoscope 5001 can be fixed more certainly without hands, and therefore, an image of a surgical region can be obtained stably and surgery can be performed smoothly.

It is to be noted that the arm controlling apparatus 5045 may not necessarily be provided on the cart 5037. Further, the arm controlling apparatus 5045 may not necessarily be a single apparatus. For example, the arm controlling apparatus 5045 may be provided in each of the joint portions 5033a to 5033c of the arm unit 5031 of the supporting arm apparatus 5027 such that the plurality of arm controlling apparatus 5045 cooperate with each other to implement driving control of the arm unit 5031.

(Light Source Apparatus)

The light source apparatus 5043 supplies irradiation light upon imaging of a surgical region to the endoscope 5001. The light source apparatus 5043 includes a white light source which includes, for example, an LED, a laser light source or a combination of them. In this case, where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 5043. Further, in this case, if laser beams from the respective RGB laser light sources are irradiated time-divisionally on an observation target and driving of the image pickup elements of the camera head 5005 is controlled in synchronism with the irradiation timings, then images individually corresponding to the R, G and B colors can be picked up time-divisionally. According to the method just described, a color image can be obtained even if a color filter is not provided for the image pickup element.

Further, driving of the light source apparatus 5043 may be controlled such that the intensity of light to be outputted is changed for each predetermined time. By controlling driving of the image pickup element of the camera head 5005 in synchronism with the timing of the change of the intensity of light to acquire images time-divisionally and synthesizing the images, an image of a high dynamic range free from underexposed blocked up shadows and overexposed highlights can be created.

Further, the light source apparatus 5043 may be configured to supply light of a predetermined wavelength band ready for special light observation. In special light observation, for example, by utilizing the wavelength dependency of absorption of light in a body tissue to irradiate light of a narrower band in comparison with irradiation light upon ordinary observation (namely, white light), narrow band light observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 5043 can be configured to supply such narrowband light and/or excitation light suitable for special light observation as described above.

(Camera Head and CCU)

Functions of the camera head 5005 of the endoscope 5001 and the CCU 5039 are described in more detail with reference to FIG. 2. FIG. 2 is a block diagram depicting an example of a functional configuration of the camera head 5005 and the CCU 5039 depicted in FIG. 1.

Referring to FIG. 2, the camera head 5005 has, as functions thereof, a lens unit 5007, an image pickup unit 5009, a driving unit 5011, a communication unit 5013 and a camera head controlling unit 5015. Further, the CCU 5039 has, as functions thereof, a communication unit 5059, an image processing unit 5061 and a control unit 5063. The camera head 5005 and the CCU 5039 are connected to be bidirectionally communicable to each other by a transmission cable 5065.

First, a functional configuration of the camera head 5005 is described. The lens unit 5007 is an optical system provided at a connecting location of the camera head 5005 to the lens barrel 5003. Observation light taken in from a distal end of the lens barrel 5003 is introduced into the camera head 5005 and enters the lens unit 5007. The lens unit 5007 includes a combination of a plurality of lenses including a zoom lens and a focusing lens. The lens unit 5007 has optical properties adjusted such that the observation light is condensed on a light receiving face of the image pickup element of the image pickup unit 5009. Further, the zoom lens and the focusing lens are configured such that the positions thereof on their optical axis are movable for adjustment of the magnification and the focal point of a picked up image.

The image pickup unit 5009 includes an image pickup element and disposed at a succeeding stage to the lens unit 5007. Observation light having passed through the lens unit 5007 is condensed on the light receiving face of the image pickup element, and an image signal corresponding to the observation image is generated by photoelectric conversion of the image pickup element. The image signal generated by the image pickup unit 5009 is provided to the communication unit 5013.

As the image pickup element which is included by the image pickup unit 5009, an image sensor, for example, of the complementary metal oxide semiconductor (CMOS) type is used which has a Bayer array and is capable of picking up an image in color. It is to be noted that, as the image pickup element, an image pickup element may be used which is ready, for example, for imaging of an image of a high resolution equal to or not less than 4K. If an image of a surgical region is obtained in a high resolution, then the surgeon 5067 can comprehend a state of the surgical region in enhanced details and can proceed with the surgery more smoothly.

Further, the image pickup element which is included by the image pickup unit 5009 includes such that it has a pair of image pickup elements for acquiring image signals for the right eye and the left eye compatible with 3D display. Where 3D display is applied, the surgeon 5067 can comprehend the depth of a living body tissue in the surgical region more accurately. It is to be noted that, if the image pickup unit 5009 is configured as that of the multi-plate type, then a plurality of systems of lens units 5007 are provided corresponding to the individual image pickup elements of the image pickup unit 5009.

The image pickup unit 5009 may not necessarily be provided on the camera head 5005. For example, the image pickup unit 5009 may be provided just behind the objective lens in the inside of the lens barrel 5003.

The driving unit 5011 includes an actuator and moves the zoom lens and the focusing lens of the lens unit 5007 by a predetermined distance along the optical axis under the control of the camera head controlling unit 5015. Consequently, the magnification and the focal point of a picked up image by the image pickup unit 5009 can be adjusted suitably.

The communication unit 5013 includes a communication apparatus for transmitting and receiving various kinds of information to and from the CCU 5039. The communication unit 5013 transmits an image signal acquired from the image pickup unit 5009 as RAW data to the CCU 5039 through the transmission cable 5065. Thereupon, in order to display a picked up image of a surgical region in low latency, preferably the image signal is transmitted by optical communication. This is because, upon surgery, the surgeon 5067 performs surgery while observing the state of an affected area through a picked up image, it is demanded for a moving image of the surgical region to be displayed on the real time basis as far as possible in order to achieve surgery with a higher degree of safety and certainty. Where optical communication is applied, a photoelectric conversion module for converting an electric signal into an optical signal is provided in the communication unit 5013. After the image signal is converted into an optical signal by the photoelectric conversion module, it is transmitted to the CCU 5039 through the transmission cable 5065.

Further, the communication unit 5013 receives a control signal for controlling driving of the camera head 5005 from the CCU 5039. The control signal includes information relating to image pickup conditions such as, for example, information that a frame rate of a picked up image is designated, information that an exposure value upon image picking up is designated and/or information that a magnification and a focal point of a picked up image are designated. The communication unit 5013 provides the received control signal to the camera head controlling unit 5015. It is to be noted that also the control signal from the CCU 5039 may be transmitted by optical communication. In this case, a photoelectric conversion module for converting an optical signal into an electric signal is provided in the communication unit 5013. After the control signal is converted into an electric signal by the photoelectric conversion module, it is provided to the camera head controlling unit 5015.

It is to be noted that the image pickup conditions such as the frame rate, exposure value, magnification or focal point are set automatically by the control unit 5063 of the CCU 5039 on the basis of an acquired image signal. In other words, an auto exposure (AE) function, an auto focus (AF) function and an auto white balance (AWB) function are incorporated in the endoscope 5001.

The camera head controlling unit 5015 controls driving of the camera head 5005 on the basis of a control signal from the CCU 5039 received through the communication unit 5013. For example, the camera head controlling unit 5015 controls driving of the image pickup element of the image pickup unit 5009 on the basis of information that a frame rate of a picked up image is designated and/or information that an exposure value upon image picking up is designated. Further, for example, the camera head controlling unit 5015 controls the driving unit 5011 to suitably move the zoom lens and the focus lens of the lens unit 5007 on the basis of information that a magnification and a focal point of a picked up image are designated. The camera head controlling unit 5015 may further include a function for storing information for identifying the lens barrel 5003 and/or the camera head 5005.

It is to be noted that, by disposing the components such as the lens unit 5007 and the image pickup unit 5009 in a sealed structure having high airtightness and waterproof, the camera head 5005 can be provided with resistance to an autoclave sterilization process.

Now, a functional configuration of the CCU 5039 is described. The communication unit 5059 includes a communication apparatus for transmitting and receiving various kinds of information to and from the camera head 5005. The communication unit 5059 receives an image signal transmitted thereto from the camera head 5005 through the transmission cable 5065. Thereupon, the image signal may be transmitted preferably by optical communication as described above. In this case, for the compatibility with optical communication, the communication unit 5059 includes a photoelectric conversion module for converting an optical signal into an electric signal. The communication unit 5059 provides the image signal after conversion into an electric signal to the image processing unit 5061.

Further, the communication unit 5059 transmits, to the camera head 5005, a control signal for controlling driving of the camera head 5005. The control signal may also be transmitted by optical communication.

The image processing unit 5061 performs various image processes for an image signal in the form of RAW data transmitted thereto from the camera head 5005. The image processes include various known signal processes such as, for example, a development process, an image quality improving process (a bandwidth enhancement process, a super-resolution process, a noise reduction (NR) process and/or an image stabilization process) and/or an enlargement process (electronic zooming process). Further, the image processing unit 5061 performs a detection process for an image signal in order to perform AE, AF and AWB.

The image processing unit 5061 includes a processor such as a CPU or a GPU, and when the processor operates in accordance with a predetermined program, the image processes and the detection process described above can be performed. It is to be noted that, where the image processing unit 5061 includes a plurality of GPUs, the image processing unit 5061 suitably divides information relating to an image signal such that image processes are performed in parallel by the plurality of GPUs.

The control unit 5063 performs various kinds of control relating to image picking up of a surgical region by the endoscope 5001 and display of the picked up image. For example, the control unit 5063 generates a control signal for controlling driving of the camera head 5005. Thereupon, if image pickup conditions are inputted by the user, then the control unit 5063 generates a control signal on the basis of the input by the user. Alternatively, where the endoscope 5001 has an AE function, an AF function and an AWB function incorporated therein, the control unit 5063 suitably calculates an optimum exposure value, focal distance and white balance in response to a result of a detection process by the image processing unit 5061 and generates a control signal.

Further, the control unit 5063 controls the display apparatus 5041 to display an image of a surgical region on the basis of an image signal for which image processes have been performed by the image processing unit 5061. Thereupon, the control unit 5063 recognizes various objects in the surgical region image using various image recognition technologies. For example, the control unit 5063 can recognize a surgical tool such as forceps, a particular living body region, bleeding, mist when the energy treatment tool 5021 is used and so forth by detecting the shape, color and so forth of edges of the objects included in the surgical region image. The control unit 5063 causes, when it controls the display unit 5041 to display a surgical region image, various kinds of surgery supporting information to be displayed in an overlapping manner with an image of the surgical region using a result of the recognition. Where surgery supporting information is displayed in an overlapping manner and presented to the surgeon 5067, the surgeon 5067 can proceed with the surgery more safety and certainty.

The transmission cable 5065 which connects the camera head 5005 and the CCU 5039 to each other is an electric signal cable ready for communication of an electric signal, an optical fiber ready for optical communication or a composite cable ready for both of electrical and optical communication.

Here, while, in the example depicted, communication is performed by wired communication using the transmission cable 5065, the communication between the camera head 5005 and the CCU 5039 may be performed otherwise by wireless communication. Where the communication between the camera head 5005 and the CCU 5039 is performed by wireless communication, there is no necessity to lay the transmission cable 5065 in the surgery room.

Therefore, such a situation that movement of medical staff in the surgery room is disturbed by the transmission cable 5065 can be eliminated.

An example of the endoscopic surgery system 5000 to which the technology according to an embodiment of the present disclosure can be applied has been described above. It is to be noted here that, although the endoscopic surgery system 5000 has been described as an example, the system to which the technology according to an embodiment of the present disclosure can be applied is not limited to the example. For example, the technology according to an embodiment of the present disclosure may be applied to a soft endoscopic system for inspection or a microscopic surgery system.

The technology according to an embodiment of the present disclosure can be applied suitably to the control unit 5063 from among the components described hereinabove. Specifically, the technology according to an embodiment of the present disclosure relates to endoscopy and/or microscopy. By applying the technology according to an embodiment of the present disclosure to the endoscopy and/or microscopy technology, the location of the endoscope and/or microscope may be found more easily. This enables the surgery to be performed with a higher degree of safety and certainty.

Endoscope Localisation Techniques

To aid navigation and give endoscopic images context, passive and active techniques exist. Passive techniques attempt to use the image data generated by the endoscope to determine the internal location within the patient. This is usually achieved through the registration of pre-operative images or 3D models. This requires for the acquisition of pre-operative images which adds to the cost and complexity of a procedure. This may also increase the risk to the patient of having further pre-operative procedures. Additionally, as tissue moves over time, image registration may be confounded by the tissue movement between the pre-operative images and the images captured during the endoscopy.

Active techniques include magnetic imaging. In this, a second device (the magnetic imager) is provided to show a real-time 3D localisation of the endoscope. This technique is for inexperienced operators and requires a large amount of additional surgical equipment to be placed in the operating theatre. This increases costs and time of a procedure dramatically.

Other information may be used. For example, insertion depth, rotational data and flexible endoscope conformation can be tracked and tagged to images for procedures such as colonoscopies, but information such as this is unreliable for anatomical image location due to the deformability of internal structures within the body.

There is a need to provide an improved localisation technique for not only endoscopes but for other surgical devices such as microscopy.

In order to improve the localisation, the distance and/or direction to other internal organs may be found. Generally, this is achieved by accentuating small changes in colour and/or movement of tissue within the captured image. This enables the distance and/or direction to that internal organ to be determined. Further, other localised physiological features may be established. For example, any localised cuts, bleed points or blood congestion may be established.

Figure 4:
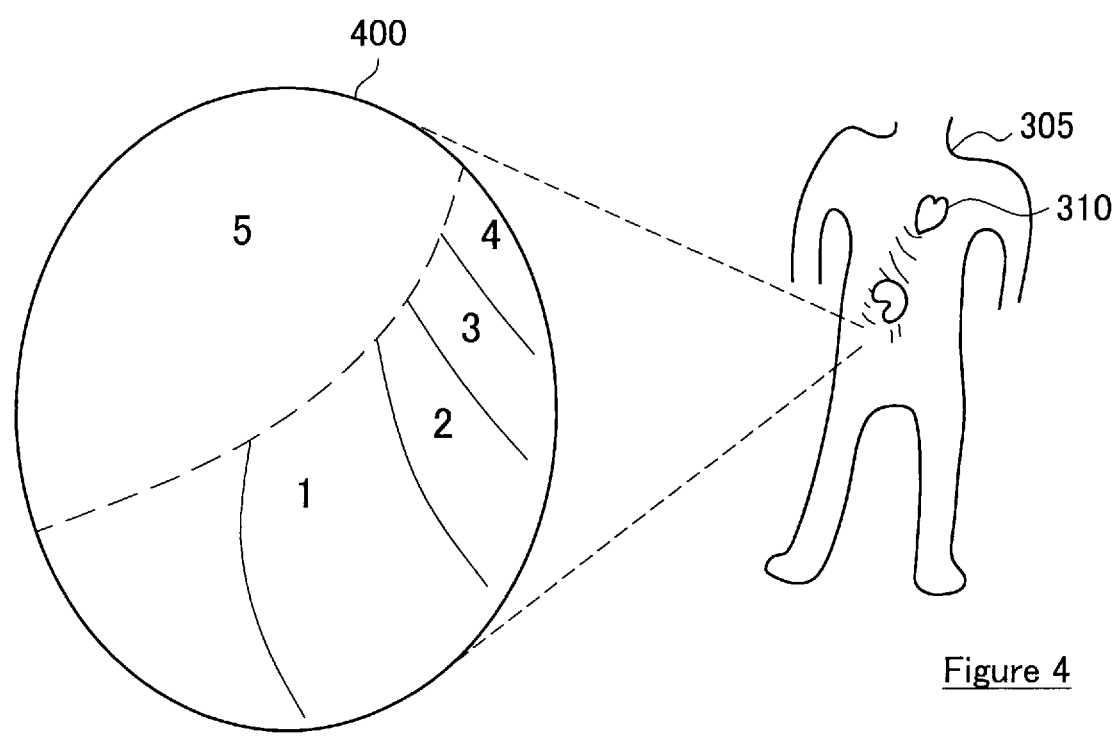

An example of the effect of this is shown in FIGS. 3 and 4.

In FIG. 1, the patient 5071 is undergoing a surgical procedure such as a colonoscopy. Although the patient 5071 is shown as a human, the disclosure is not so limited and the surgery may apply to any branch of medicine, for example, veterinary medicine.

The image from the surgical device (which may be an endoscope, but may also be a microscope) according to embodiments is shown in 300. Normally, this image would include few landmarks as explained in the introduction. However, in FIG. 3, there are pulse waves which are labelled 1-4. These pulse waves are caused by the heart 310 of the patient 5071 beating. In particular, the beating of the heart causes very small ripples which are imperceptible to the naked eye along the surface of the colon. This is because the heart applies a mechanical motion to the body when it moves. This mechanical motion generates a mechanical wave front that traverses the soft tissue within the patient's body. As the mechanical motion is quite small, at a relatively small distance from the heart, the amplitude of the mechanical wave front is imperceptible to the human eye. However, in embodiments of the disclosure, image processing is carried out on the endoscope image to accentuate the oscillatory motion in the image. This emphasises the ripples as shown as the wave fronts in FIG. 3 which would normally be imperceptible to the human eye. Of course, although the example discusses a heart-beat as the cause of the ripple, the disclosure is not so limited. In particular, any organ that applies a mechanical movement on the body such as lungs that physically move may also cause ripples.

The image 300 of FIG. 3 consists of four wave fronts. It will be appreciated that the wave-fronts are travelling in the direction shown by the arrow 315 in FIG. 3. In other words, the wave-fronts are moving in the direction away from the heart 310. In order to capture the image, there are two pieces of image processing carried out. The first piece of image processing is the generation of the wave front in the image. This is achieved by accentuating the oscillatory motion in the image. In other words, image processing is carried out which emphasises the mechanical motion (the wave fronts or ripples) caused by the movement of the heart.

In order to achieve this, in embodiments, Eulerian video processing is carried out on the captured image. Eulerian processing is one of several image processing techniques which decomposes each image into spatial frequency bands. The same temporal filter is then applied to each spatial frequency band and the filtered spatial frequency band is amplified by a predetermined amount. In other words, the goal of the process is to amplify temporal changes in the image within certain temporal frequency bands (i.e. apply a bandpass temporal amplification) to reveal oscillatory changes of intensity/colour in a static patch of an image or accentuate oscillatory motion of an object within an area of the image. It should be noted that Eulerian video processing is particularly useful when compared to Lagrangian approaches as Eulerian video processing magnifies small motion in the presence of larger motion (which is useful in surgery where endoscopes and internal organs move). A "Brief Description of Eulerian Video Processing" is provided later.

Determining Location of Endoscope Relative to a Physiological Features

Returning now to FIG. 3, after Eulerian video processing has been applied to the captured images, the first of the four wave fronts of FIG. 3 will be identified. In embodiments, the Eulerian image processing is carried out in the image processing unit 5061 which is comprised of circuitry. Of course, the disclosure is not so limited and the image processing may be carried out anywhere in the CCU 539 or indeed in the camera head 5005. Over a short predetermined period of time (for example, 500 ms) the amplitude changes of the tissue surface between captured frames is analysed. This allows the oscillatory changes to be identified and to be extracted. The frequency of oscillation over the time period is determined using a transform function such as wavelet or Fourier transforms.

Although not necessary (as will be explained later), if the amplitude is used to determine the distance, the resolution of the measurement of the amplitude would be linked to the resolution of the imaging system. The Eularian amplification technique is able to detect and resolve movements that are smaller than a single pixel (down to $1/100^{th}$ of a pixel) so is able to resolve the amplitude of small motions better than other motion detection techniques. Furthermore, only relative amplitude is required for embodiments of the disclosure. For example, comparisons between different image areas will provide a comparative difference of amplitude identifying the timing and relative amplitude difference between ventricular and atrial contractions.

These mechanical oscillations on the surface can be separated from other oscillation caused, by for example, the patient breathing or other tissue movement caused by the endoscope. This separation is achieved using Heart Oscillation Reference data (stored in storage accessible by the image processing unit 5061) where known ranges of periodicity, amplitude, frequency and dynamic profile of the heart beat within humans at rest are used to extract wave-fronts associated with the heart-beat. This may be performed after the Eulerian video processing or may be performed as part of the Eulerian video processing. For example, the temporal amplification step in the Eulerian video processing may be carried out at typical heart beat frequencies.

Although apparent to the skilled person, the term "dynamic profile" in this context refers to the repeating pattern of mechanical vibrations caused by the multiple chambers of the heart beating in sequence. More specifically, this will be the characteristic frequency and amplitude changes that occur in the waveform over time. For example, this may be a known allowable range of amplitude or frequency ratios between the ventricular and atrial contractions.

The timing of the Heart Oscillations occurrence in each section of the image can be determined, allowing observation of the spread of the Heart Oscillations within the image. This process is demonstrated in FIG. 3. Given knowledge of the 3D orientation of the imaged surfaces, such as through 3D modelling, the directions of spread of the oscillations across surfaces can also be determined in 3D. This is because the orientation of the patient and the endoscope is known to the endoscopic system (through use of gyroscopes on the endoscope for example). By reversing these directions, the approximate direction of the source of the Heart Oscillations can be determined.

However, due to the high speed of sound propagation in tissue relative to the frame rates of the image sensing circuitry in the image pickup unit 5007, images can be acquired in phase with the period of the heart to acquire multiple stages of wave propagation within the image. In other words, the frame rate of the image sensor circuitry may be adjusted to be in phase with the heartbeat of the patient. The heart beat may be determined from the ECG or by other means.

An approximation as to the distance to the heart is then determined by the CCU 5039 (which comprises circuitry) by the difference in the time of arrival of the Heart Oscillations versus the corresponding pulse wave of blood (determined by the change in colour obtained using Eulerian processing as explained later) in the visible blood vessels, and their estimated speeds. These estimated speeds are determined from known speed values for sound and pulse wave velocity in soft tissue and arteries. These values may be obtained during a training phase. The training phase is explained below in the section entitled "Training Phase for Intervening Objects and Tissue Samples"

Assuming a direct propagation path, the distance to the common origin of both signals can be determined by multiplying the ratio of speeds by the difference in arrival time within the image.

Alternately, the distance may be determined by comparison with a separate recording of either the patient's pulse or mechanical vibrations of the heart at a known distance from the heart. In other words, it is not essential that the change is colour is required in order to determine the distance to the heart. Specifically, during the training phase, the location of the endoscope is continually recorded along with the corresponding parameters of the wave front and (optionally) the colour change. During use, the parameters of the wave-front are used to determine the location of the endoscope by comparing the stored parameters and optionally colour change with the stored parameters and (optionally) colour change.

In order to improve the estimation of the distance between the endoscope and the heart, the estimation may be combined with other methods of distance estimation such as depth of insertion methods.

The broadening of the frequency spectrum and the separation of the frequency components in time can be determined by comparison with a similar measurement of Heart Oscillations from an image of the patient's chest above the heart. These changes to the frequency profile are an indicator of non-linear propagation, the effect of which increases with propagation distance.

This provides a method of estimating the distance a signal has traveled through the body that may be used in combination with the other described methods.

A reference measurement of the frequency components of the heart mechanical waveform may be made for example by analysing a video taken of the patient's chest above the heart. Measurements of the mechanical waveform that are then made from other locations can be compared against this to determine the degree of change at the measurement site that has occurred and therefore an estimate of the distance traveled.

Alternately, if there is little inter-patient variation in heart beat frequency dynamics in the Oscillation Reference Data, a comparison may be made with reference data of oscillation spectra and dynamics taken close to the heart.

Although the foregoing describes the identification of the endoscope relative to the user's heart (or lungs) using mechanical motion only applied to soft tissue, the disclosure is not so limited. For example, the foregoing may be applied to detecting the location of any physiological feature. A physiological feature is any feature located within the human anatomy. An example of this is a cut, a bleed point, blood congestion or the like or an internal organ.

As briefly noted above, in embodiments, the accentuation of imperceptible colour changes in an image may be used instead of or in addition to those described above with respect to mechanical motion to assist in locating the endoscope with respect to the heart (or lungs).

Although the above discussed determining the location of the endoscope using the propagation of a pulse wave through soft tissue, in embodiments, the propagation of a pulse wave traveling through vasculature on the imaged surface may also be tracked. This also allows the orientation and location of the image with respect to the direction of the heart to be derived:

The contraction of the heart chambers such as the left ventricle sends a pulse wave of blood through arteries that dissipates as it travels. This causes a movement and colour change within the image as the pulse wave alters the volume of blood in the tissue periodically. These changes are imperceptible to the naked eye as the changes are typically small when the pulse wave reaches the vasculature within the imaged surface.

As in the embodiments above, these small amplitude oscillations are detected by Eulerian Video Processing whereby the minute changes of the tissue surfaces that occur between frames are analysed over a period of time, allowing the changes with an oscillatory nature to be extracted.

The frequency spectra over certain time intervals of the observed composite surface oscillations can be determined using a Fourier or wavelet transform function.

For both colour and motion, the oscillations resulting from the pulse wave are separated from the other oscillations by using reference data consisting of known heart beat frequencies, pulse wave dynamics (which may be pulse wave components corresponding to diastole and systole) and the period of the waveform. It will be understood that other examples may include any characteristic of the pulse waveform varies over time. This 'Vascular Reference Data' defines the expected ranges of these parameters that may be associated with vasculature and is stored to be accessible by the CCU 5039.

The Vascular Reference Data consists of known ranges of periodicity, change amplitude, frequency, and dynamic profile of the pulse wave within different vasculature dimensions at rest. This data may be measured from test cases representing a cross section of the population as in the case of the wave fronts for soft tissue explained above. Optionally this may be recorded from separate locations on the patient being examined.

The components of the oscillations that are within all of the expected ranges for the vasculature are grouped into 'Vascular Oscillations'.

The timing of the Vascular Oscillations occurring in each section of the image is determined, allowing observation of the spread of the pulse wave through the vasculature in the image. Given knowledge of the 3D orientation of the imaged surfaces, such as through 3D modelling approaches, the directions of spread of the Vascular Oscillations across surfaces are also determined in 3D. This is because the orientation of the patient and the endoscope is known to the endoscopic system (through use of gyroscopes on the endoscope for example). By reversing these directions, the approximate direction of the source of the Heart Oscillations can be determined.

However, due to the high speed of sound propagation in tissue relative to the frame rates of the image sensor, images can be acquired in phase with the period of the heart to acquire multiple stages of wave propagation within the image. In other words, the frame rate of the image sensor in the endoscopic system may be adjusted to be in phase with the heartbeat of the patient. The heart beat may be determined from the ECG or by other means.

In some scenes, blood flow direction may be dependent on the nearest branch from a major artery, which may be significantly different from the direction towards the heart. In this case, other heart location cues such as the mechanical motion mechanism where the ripple caused by the beating of the heart described above may be used to mitigate this inaccuracy.

Determining Structures Between Heart and Endoscope

Referring to FIG. 4, embodiments of the disclosure are shown. Similarly to FIG. 3, where like numerals refer to like features, the endoscope is performing a colonoscopy. In this instance, however, the image 400 captured by the endoscope includes the wave fronts of FIG. 3 and an area 5. The area 5 includes no wave-fronts in this example.

Area 5 is created by the wave front emanating from the heart 310 being obscured by, in one example, the stomach 405. In other words, in embodiments of the disclosure, the presence of the stomach 405 (which itself produces no motion) between the endoscope and the heart 310 produces a so-called differential heart oscillation. The area 5 may have no wave front or may have different wave fronts to those described with reference to FIG. 3 above and is one example of a differential heart oscillation. In general terms, in this embodiment, the disclosure describes identifying an intervening structure which itself produces no motion, but whose presence can be identified by analysing the wave-front from an organ that does provide motion such as the heart.

In this case, intervening structures such as particular organs with differential heart or lung oscillation transfer functions may be identified by observing the oscillations of imaged surfaces that occur due to different propagation paths. For example, as shown in FIG. 4, the location of the stomach 405 may be identified by the refraction, reflection and attenuation patterns that occur when the stomach is located between the heart and an imaged surface. Although the location of the stomach may be identified, the disclosure is not so limited. Generally speaking, the differential transfer function is the effect that the intervening organ has on the oscillation signal in terms of speed, attenuation and frequency altering effects. Apart from the example of highly reflecting structures such as air spaces (which help identify the stomach), different density tissues will affect the frequency components that propagate to the measurement site and the speed at which they arrive. Given a signal where a comparison between transmission paths can be made, waveform and time of arrival analysis may be able to determine the presence of a more or less dense intervening structure in one path which could be identified as a particular organ.

Heart Oscillations are identified as described above.

In some scenes, the identified amplitude, frequency spectrum, dynamic frequency profile or spatial and temporal profile of the Heart Oscillations may be different between separate areas of the image in multiple images.

In cases of intervening structures with high reflectance such as the partially air filled stomach, the Heart Oscillation signal amplitude will be greatly reduced in a section of the imaged surface. The refraction, reflection and attenuation patterns at various points on a patient will be captured during a training phase. For example, differential motion patterns at a particular location of the endoscope such as a step time of arrival of varying frequency components of the heart motion infers different intervening structures. In addition, some intervening structures may create characteristic patterns in the signal which are unique to the structure and may be recognised if they are not repeated in other propagation paths. These characteristic patterns can be established in patients from modelling software or experimentation.

If the path length of the signal is long then it may be too difficult to separate subtle effects of some intervening organs. However, if the path length is short and the effect of the intervening organ is relatively large, such as with the stomach, the observed difference between two signal paths may be used to identify the stomach with a high degree of confidence.

Therefore, the area that is occluded by the stomach from the Heart Oscillations can be determined.

Given the known direction of the heart from the non-occluded surfaces, the direction and some boundaries of the stomach can be identified by triangulation. This can be achieved because given the known direction of incoming waves, the observed occluded area could be used to approximately define the edges of the stomach. It is appreciated that the clarity of the acoustic shadow may decline with distance from the air void, which may make the effect unnoticeable after a certain distance.

Therefore, using the time of arrival and the angle of wave propagation over the imaged surface it is possible to determine the presence of a void further away (i.e. beyond the certain distance) that the waves have refracted around. These waves could be filtered to define the obscured area. However, the angle of the waves would reduce with distance to the stomach, making this task harder with distance from it.

Figure 13:
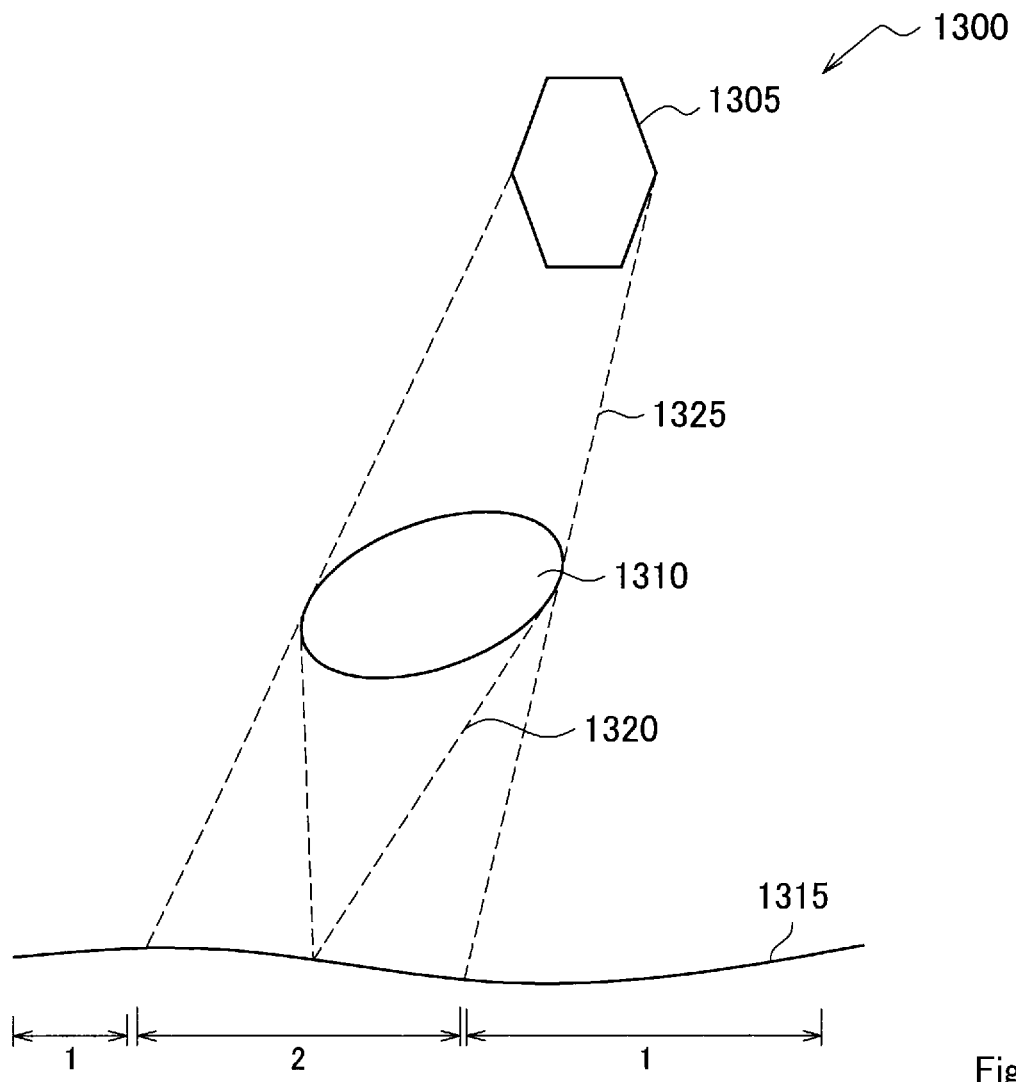
FIGS. 13 and 14 show diagrams that explain the detection of an intervening object further from the oscillating source.
Figure 14:
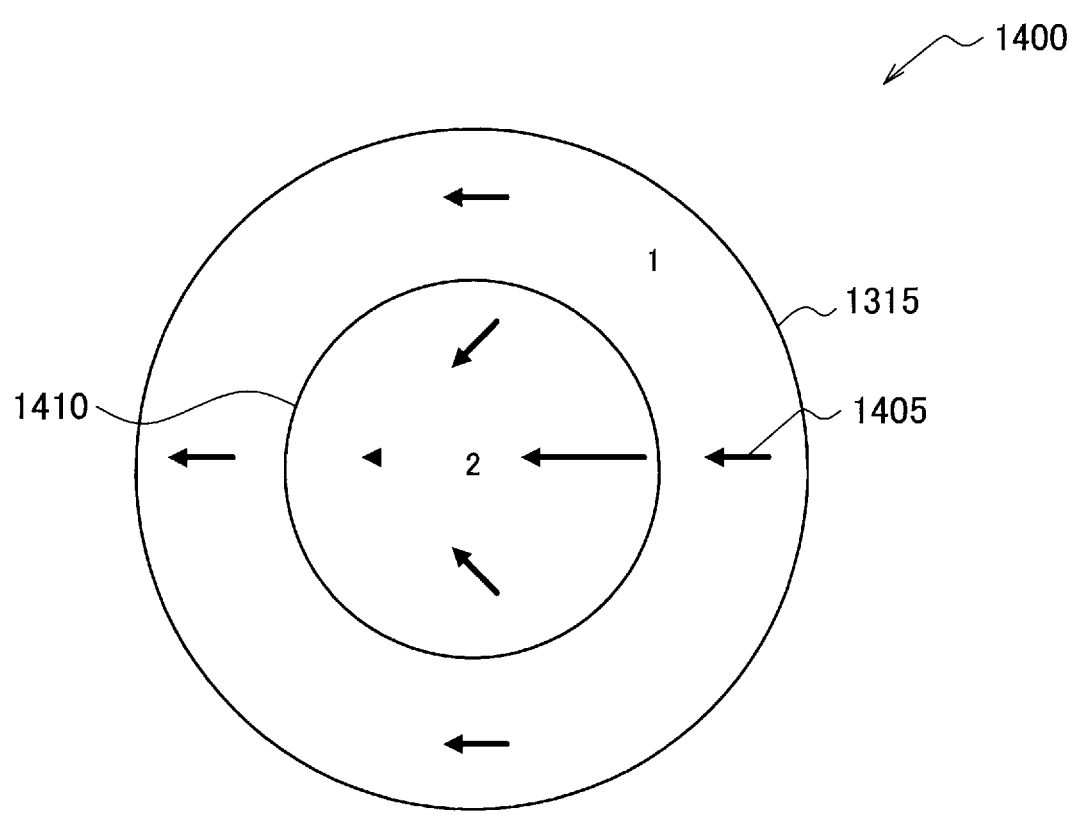

An explanation of one mechanism to measure the presence of an intervening object is given with reference to FIGS. 13 and 14. Referring to FIG. 13, an illustrative example 1300 includes a heart 1305 that produces the waves and the stomach 1310 is the occluding (intervening) object. The endoscope captures the image of the tissue surface 1315. In this case, the stomach 1310 is far from the imaged tissue surface 1315 and therefore cannot be identified easily by a shadowing effect. In this case, the presence of the stomach 1310 may be identified by relative changes in the wave time of flight.

The path length of the diffracted acoustic path 1320 shown in FIG. 13 will be longer than that of the un-occluded, direct transmission paths 1325. This leads to a progressively increasing time of flight difference towards the centre of the imaged tissue (i.e. in section 2). With sufficient temporal resolution, this pattern is perceived as the arriving waves travel over the surface with a propagation vector component towards a centre point (perpendicular to the stomach's edge), irrespective of imaged tissue orientation. The vector component would be superimposed on the wave propagation vector present in section 1 of the imaged tissue surface, which would be a function of the tissue's direct distance to the heart 1305. An example of the wave propagation vectors that may be observed in section 1 and 2 of the tissue surface 1315 is shown in FIG. 14.

In FIG. 14, an endoscope view 1400 is shown. However, in conjunction with the disclosure of FIG. 13, it is evident that even if only a small section of tissue is visible such as when the field of view 1400 of the endoscope travels over the boundary between sections 1 and 2, the difference in the directional vector of the observed wave (either wave propagation speed or direction) which is not due to tissue geometry, is used to define this boundary. Therefore, the presence of the stomach 1310 in the transmission path from the heart 1305 is identified with confidence. Similarly, by scanning the endoscope view 1315 over areas that do not contain an identifiable boundary, the different regimes of linear arrival time progression over the imaged surface or relative time of arrival changes towards a centre point is identifiable without a comparison being required.

If the endoscope view is too small to identify such features with sufficient confidence, virtual image area construction techniques may be used to measure a wider area over multiple biological (heartbeat) cycles as the endoscope is moved.

Components of the signal that are due to refraction and reflection may confound the accuracy of this boundary definition approach as there may still be signal within the directly obscured area. However, these signals can be filtered as they will be incident at different angles and timings than the direct signal from the heart and are therefore identifiable from the different direction of spread across the imaged surface as described above, and from expectations of timing given by the arrival timing on other surfaces.

Structures such as rib bones may transmit certain frequency components to the imaged surfaces efficiently due to their proximity to the heart and significantly different mechanical properties. Although this is not an intervening structure, its location may also be identified by the direction of its signal components, and could be identified with further confidence by analysing the change in the frequency components of the Heart Oscillations that occur during a breathing cycle, as the ribs are likely move significantly relative to the imaged surface.

The dynamics of the observed motion attributed to different organs such as the timing and relative amplitude of ventricular versus atrial contraction (a larger amplitude disturbance would be detected for the former), or the different motions created by the rib cage and diaphragm during breathing could be used to infer orientation and distance relative to the organ.

Although the foregoing has been described with reference to the presence of organs being detected, a similar process may be applied to determine the presence of different types of tissue.

In this case, tissue properties can be assessed using small vibrations originating from natural sources such as the heart or lungs. For example, variations in the stiffness of tissue can be detected to identify cancerous tissue. In this case, during the training phase, the impact on the oscillatory motion may be determined by performing training on cancerous tissues at similar locations to that within the patient.

Similarly, to the identification of intervening structures and organs described above, the location of a surface abnormality may be determined by image sections where the properties of the Heart Oscillations are altered.

Tumours are generally stiffer than surrounding soft tissue and therefore will respond differently to the Heart Oscillations than surrounding tissue. These altered oscillations, such as a particular shift in the frequency spectrum, can be automatically compared against reference data of possible surface tumour transfer functions. The likelihood of a particular surface abnormality being a tumour can therefore be identified. The term surface tumour transfer function is a function describing how a surface tumour impacts the Heart Oscillations. The transfer function may be measured in advance by applying a known oscillation to the tissue and determining the impact of the surface tumour on the oscillation. Of course, although the above discusses a surface tumour, any kind of intervening object such as an organ or the like is envisaged.

The boundary between the abnormality and the normal tissue may also be investigated by the geometry of the transition from normal Heart Oscillations and the localised altered oscillations. This may help determine between hard and soft edged tumours for example as well as defining the borders of the tumour.

Figure 5:
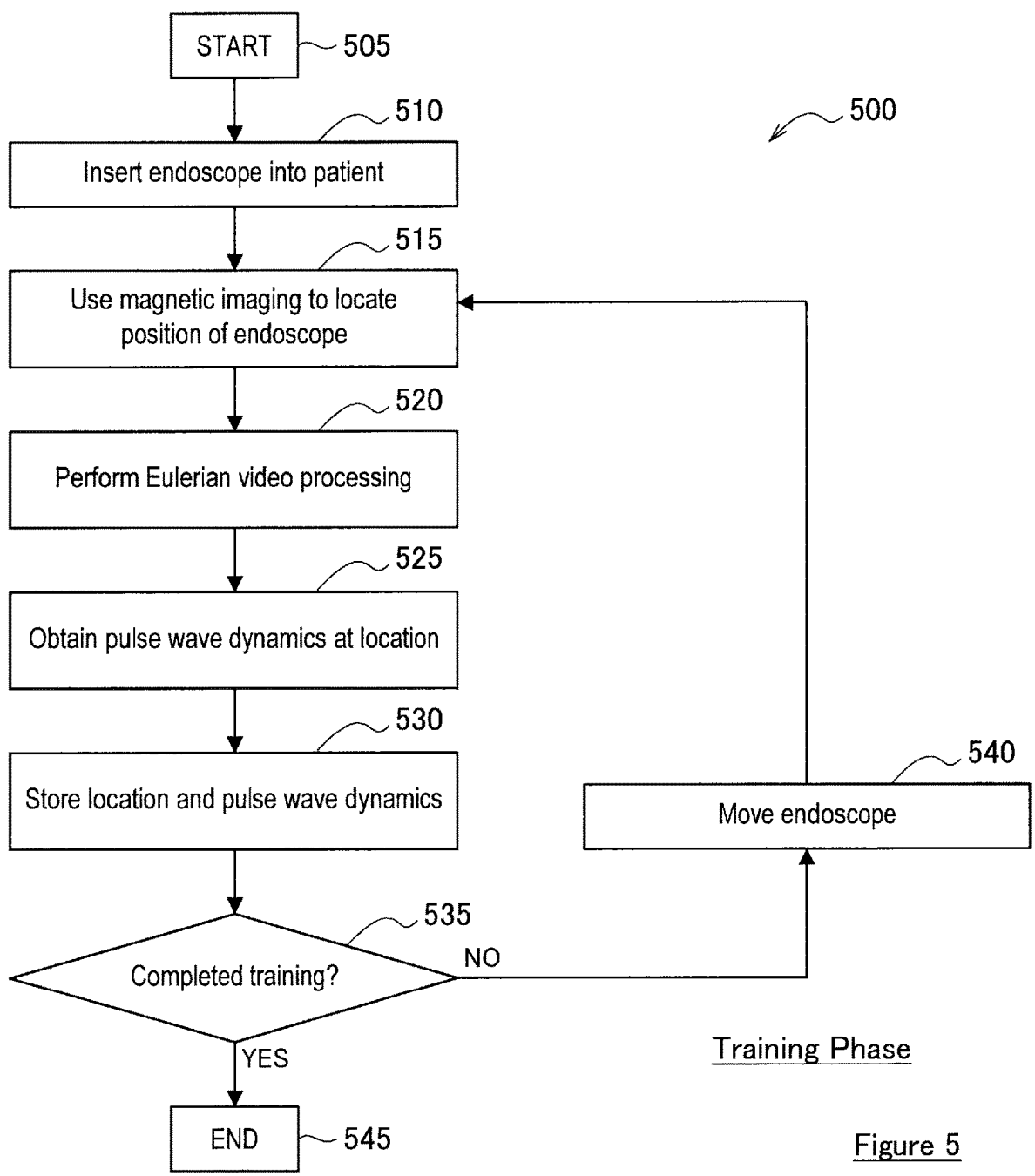
FIG. 5 is a flow diagram explaining a training phase according to embodiments of the disclosure.

Operation to Determine Location of Endoscope Relative to a Physiological Feature Referring to FIG. 5, a flow chart 500 explaining the training phase is shown. The process starts at 505. In step 510, the endoscope is inserted into the test patient. The accurate position of the endoscope is identified in step 515. This is achieved using magnetic imaging or the like. The orientation of the endoscope is also determined using a gyroscope and/or an accelerometer located in the endoscope. The captured image has Eulerian video processing performed in step 520. The Eulerian video processing accentuates the oscillatory motion. The pulse wave dynamics, such as the periodicity, size and movement of the wave front at that location are determined in step 525. In particular, the timing between wave fronts defines the periodicity. Pulse wave movement is defined by a measurement of wave speed along the vessel. Amplitude of the pulse wave is determined through a measurement of the maximum relative increase in vessel width at an arbitrary point. The obtained pulse wave dynamics are stored in association with the position of the endoscope in step 530.

In step 535, it is determined whether the training has been completed. This will typically be decided by the surgeon or endoscopy operator. In embodiments, as the capture and storage of the pulse wave dynamics is a continual procedure, the process will default to step 540 where the endoscope will be moved by the operator and the process will return to step 515.

However, once the process has completed, the surgeon will stop the process and therefore the process will end at step 545.

Figure 6:
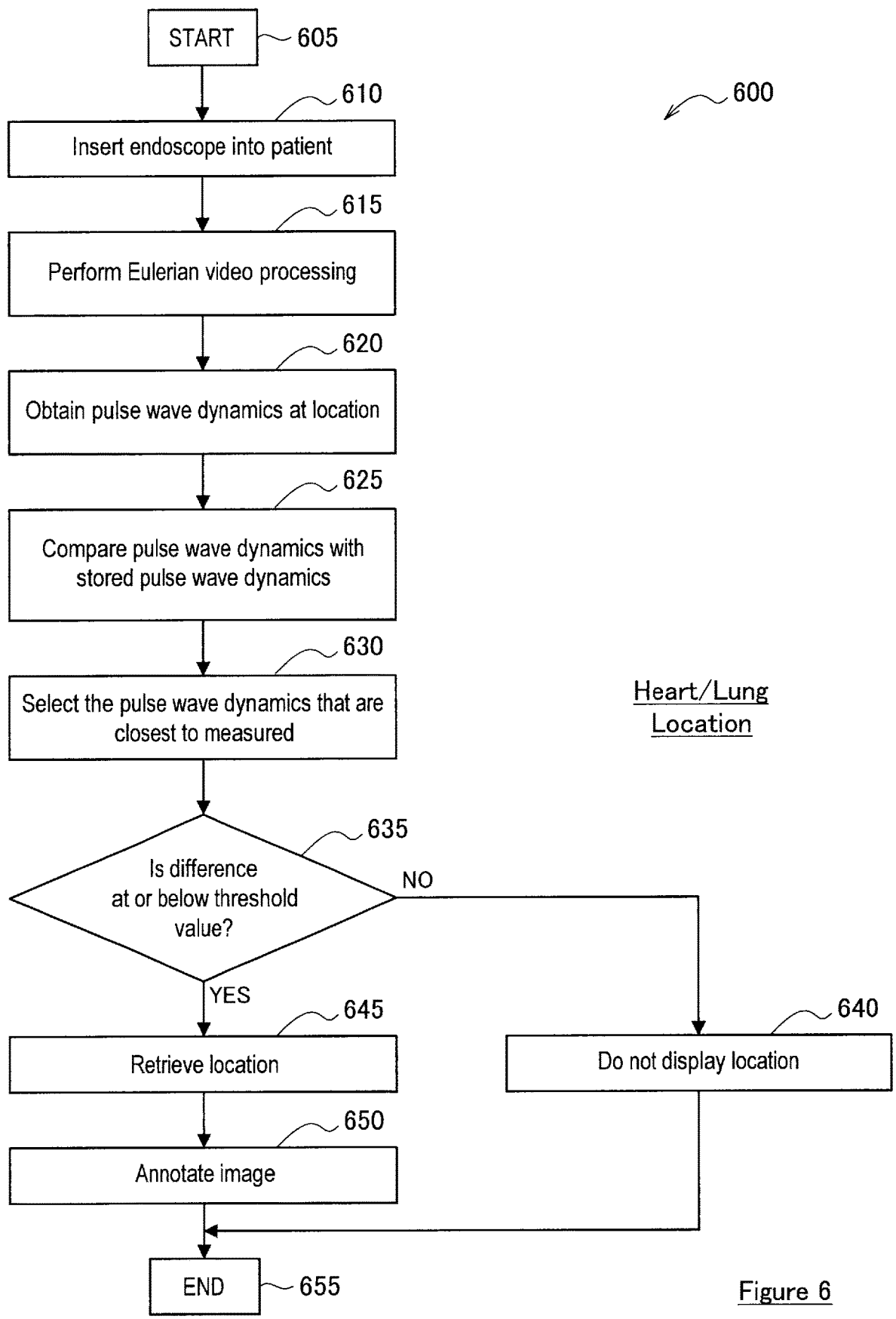
FIG. 6 is a flow diagram explaining embodiments of the disclosure.

Referring to FIG. 6, a flow chart 600 explaining the heart and/or lung location technique is described. The process starts at step 605. The process moves to step 610 where an endoscope is inserted into the patient under test.

Eulerian image processing is carried out in step 615. The pulse wave dynamics, such as the periodicity, size and movement of the wave front at that location are determined in step 620. The obtained pulse wave dynamics are compared with the stored pulse wave dynamics obtained during the training phase of FIG. 5.

It should be noted here that the periodicity is fundamental frequency of wave, the size is maximum amplitude and movement is velocity and direction. Also, the Eularian magnification amplifies motions within a defined frequency range. The same temporal amplification is used during training and testing. The data is basically the frequencies, phases and amplitudes at different positions (in this case one location). These can be alternatively viewed as the amplitude and phase of a compound wave, or equivalently amplitude, direction and velocity of a compound wave, at that position.

The stored pulse wave dynamics which are closest to the obtained pulse wave dynamics are selected in step 630. A check is then carried out in step 635 to determine the amount of difference between the stored pulse wave dynamics and the obtained pulse wave dynamics. If the difference is at or below a threshold value then the "yes" path is followed.

Alternatively, if the difference is above the threshold value, the "no" path is followed. In embodiments, the threshold value is 0.3% of the measured value. Of course, other values may be selected. The purpose of the threshold value is to determine whether the obtained location is accurate enough to indicate the position of the endoscope to the user.

If the certainty of the location is too low, then the location will not be displayed in step 640 as to display an inaccurate location to the user may complicate the procedure. The process ends at step 655 if the location is not displayed.

Returning to step 635, if the difference is at or below the threshold value, the "yes" path is followed and the location of the endoscope is retrieved from the stored location values. This is performed in step 645.

As the endoscopic system retrieves the location of the endoscope, the relative distance (and direction) between the heart (or lungs) and the endoscope may be established. The relative distance and direction may then be overlaid onto the captured image to be displayed to the operator of the endoscope. An example of the overlaid image is shown in FIG. 7.

The process then ends at step 655.

Figure 7:
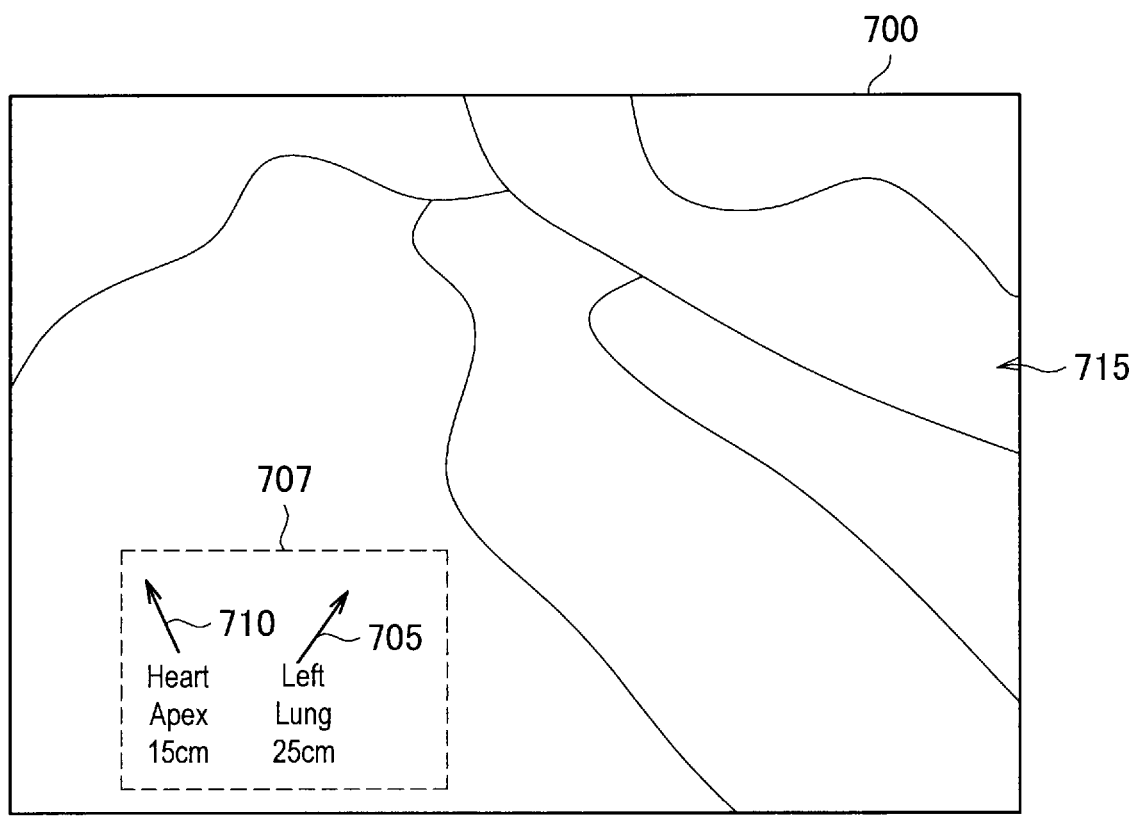
FIG. 7 is an endoscope view explaining embodiments of the disclosure.

Referring to FIG. 7, the overlaid image 700 includes an image 715 from the endoscope and context information 707. In the example of FIG. 7, the context information 707 includes an indication to the heart 710 and an indication to the lung 705. The context information may be provided anywhere on the image. For example, the context information may be provided at the bottom of the image to avoid minimise the amount of endoscopic image obscured by the context information. Further, the colour and size of the context information may be selected to minimise the amount of endoscopic image obscured whilst ensuring that the impact of the context information is high.

Determining Landmarks

As noted above, landmarks are placed within the patient's body during endoscopy to allow the surgeon or endoscopy operator to locate or relocate areas of interest. This is typically either a tattoo or a suction cup mark. The mark may be placed relative to an anatomical feature such as an organ, but this is not necessary.

Two problems exist with current techniques for landmarking. The first is that surgeons typically place the landmarks at uniform distances along the path of travel. This allows the surgeon to gauge the distance they have traveled. This is achieved by counting the number of marks passed and measuring the elapsed time. The sensation of moving, however, is dependent upon the distance to the object being viewed. This may result in inaccurate distance estimation and non-uniform landmarks.

The second problem is that during procedures, anatomical features move and so landmarks placed on the surface of the tissue (such as tattoo or suction cup) become less effective.

It is an aim of embodiments of the disclosure to address these issues.

The first problem associated with landmarking is primarily dealt with using the technique described above where the relative distance between the endoscope and the heart or lungs is determined using Eulerian video processing. This is because the distance moved is determined independently of the distance from the object being viewed. The technique described above may therefore be used to create landmarks at a uniform spacing.

The second problem uses the relationship of the features comprising the landmark rather than the visual appearance of a landmark. In embodiments, the landmark used is the vasculature.

Figure 8:
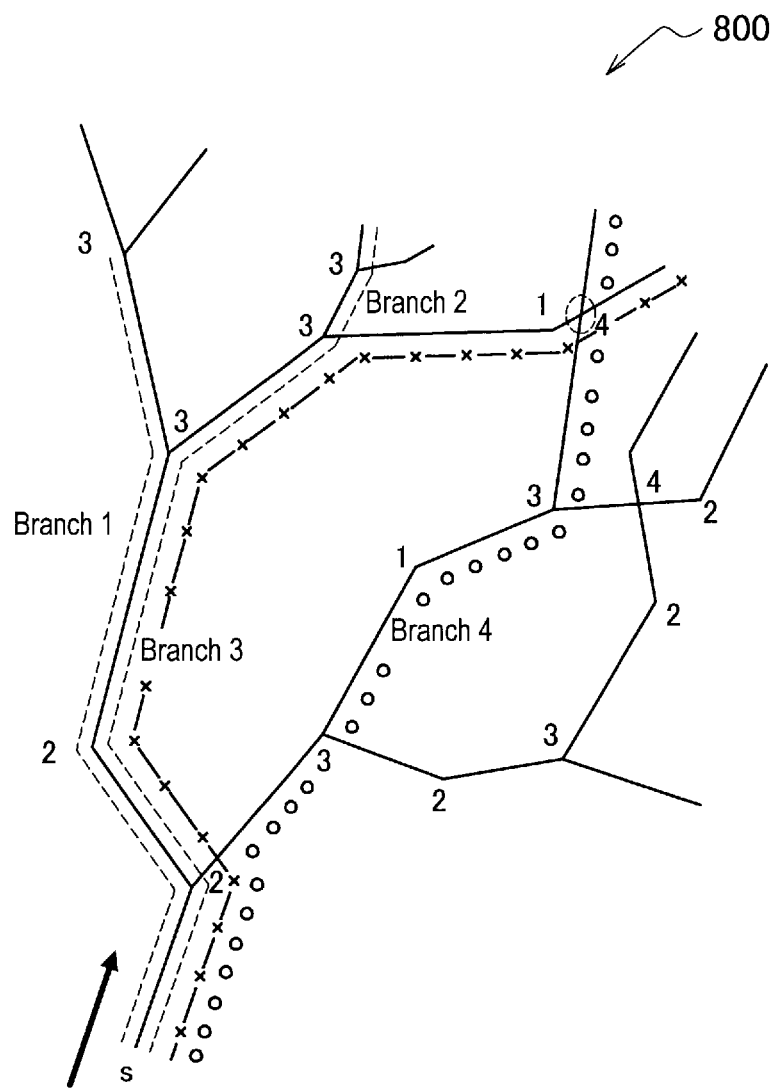
FIGS. 8 to 10 show vasculature branches explaining embodiments according to the disclosure.

A topographical landmark is explained with reference to FIG. 8. In FIG. 8, a vasculature 800 is shown. In order to identify landmark 'S', the branching of the vasculature is used. Specifically, 'nodes' consisting of branch points or cross-overs, are classified by the number of vascular channels leading to/from them. The "branches" are then defined as a series of connected nodes, originating from the same origin node that the user wishes to mark; in this case, location 'S'. These branches are used to uniquely identify location 'S'.

In the example of FIG. 8, four branches are shown identifying the position of location 'S'. The branch numbers and numbering system is shown in FIG. 8. Specifically, location 'S' consists of 4 different branch systems, branch system 1-4. The branch systems are defined by the branches entering or leaving a node. So, in the example vasculature 800, branch system 1 is composed of branch 2, 2, 3, 3: branch system 2 is composed of branch 2, 2, 3, 3: branch system 3 is composed of branch 2, 2, 3, 3, 1, 4 and branch system 4 is composed of branch 2, 3, 1, 3, 4.

In order to identify location 'S', the vasculature branch system is composed of a pattern. This pattern would be identified using known pattern matching techniques, such as the multi-point closeness of fit. Therefore, when the user identifies location 'S' as a landmark using a user interface, the vasculature branching associated with the landmark is captured. Accordingly, when the endoscope visits location 'S' again, the vasculature branching system is identified using pattern matching and the user is notified that they are currently in location 'S'. If multi-point closeness of fit is used, the likelihood of the pattern captured in the image being the known location 'S' is determined.

Therefore, as the location of the landmark (location 'S') is determined by the vasculature, even if the surface were to deform, the nature of the vasculature branching would remain constant. Therefore, the landmark is resistant to such deformation.

In addition it is envisaged that the user may also remove landmarks that are no longer required. For example, should the user not require notifying of location 'S', they may use a user interface to delete the stored vasculature branching associated with the location. Accordingly, the user will not be notified of location 'S' as a landmark. This is useful to save storage and to avoid alerting the user when not necessary. Of course, other mechanisms to decide when to delete a previously stored landmark exist. For example, when setting a landmark, an importance level may be set. The importance level sets the level of importance to the surgeon of the landmark. Accordingly, an old landmark may be automatically deleted when the surgeon identified when the new landmark as being of greater importance than the old landmark.

Figure 9:
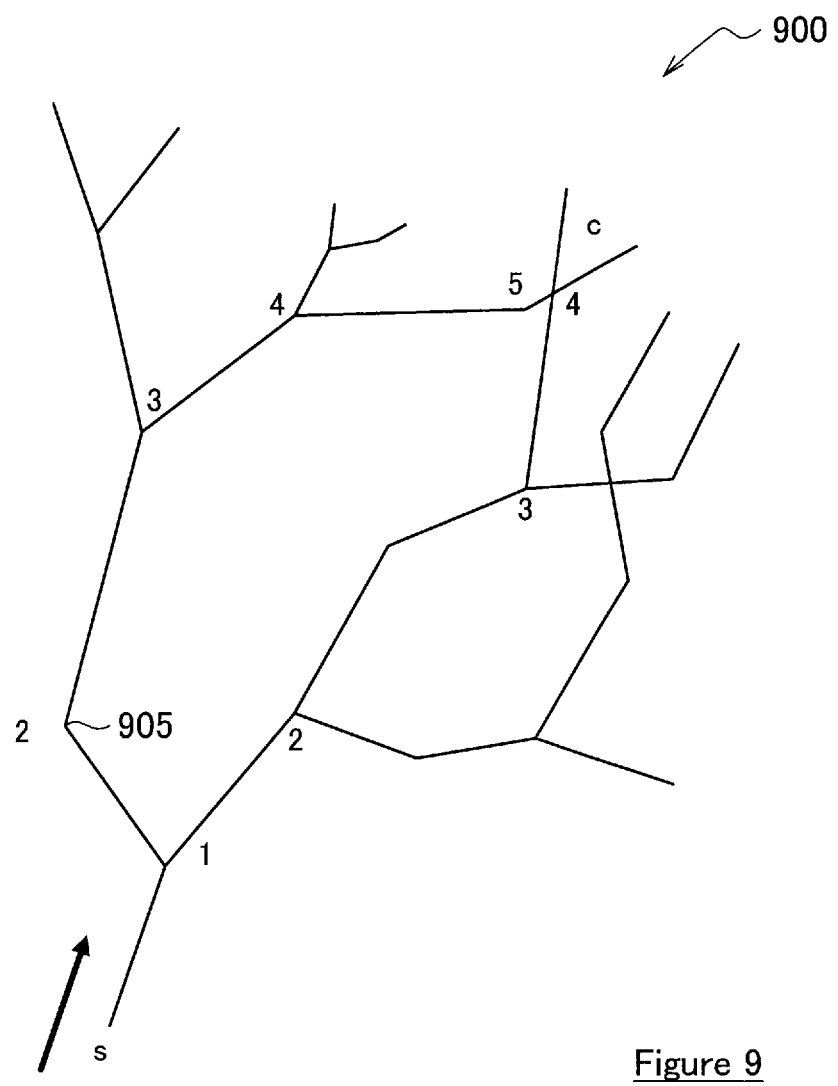

A further topographical landmark is explained with reference to FIG. 9 where the numbers on the vasculature 900 represent units of time, such as milliseconds. In FIG. 9, the same vasculature of FIG. 8 is shown. However, in the vasculature of FIG. 8, the endoscope operator (such as the surgeon) must view the vasculature. In the embodiment of FIG. 9, however, the landmarks may become partially obscured during procedures which would inhibit their recognition.

In order to address this, a dynamic landmark is provided. In a dynamic landmark, two vascular branches that have a common origin and later observable nodes are identified. The time taken for a pulse wave to travel from the shared branch point to each node is measured for each branch and used as a dynamic landmark. When returning to the landmark, even if either branch is partially obscured or deformed, the branches may be identified by the relative pulse wave timings at the visible nodes.

The rate of pulse wave amplitude dissipation within vessels and the reductions that occur at branch points may be used in a similar manner to the timing information, to identify specific branches even if they are partially obscured. For example, if the second node 905 in branch 1, shown in FIG. 9, is obscured, the number of times the vessel has branched can be estimated from the reduction in pulse wave amplitude between the first and third node, thereby recovering the missing branch information. The pulse wave amplitude is measured using the Eulerian Processing explained above. In some instances, and without prior knowledge, it may be possible to identify that there has been at least one branch that has not been observed.

Figure 10:
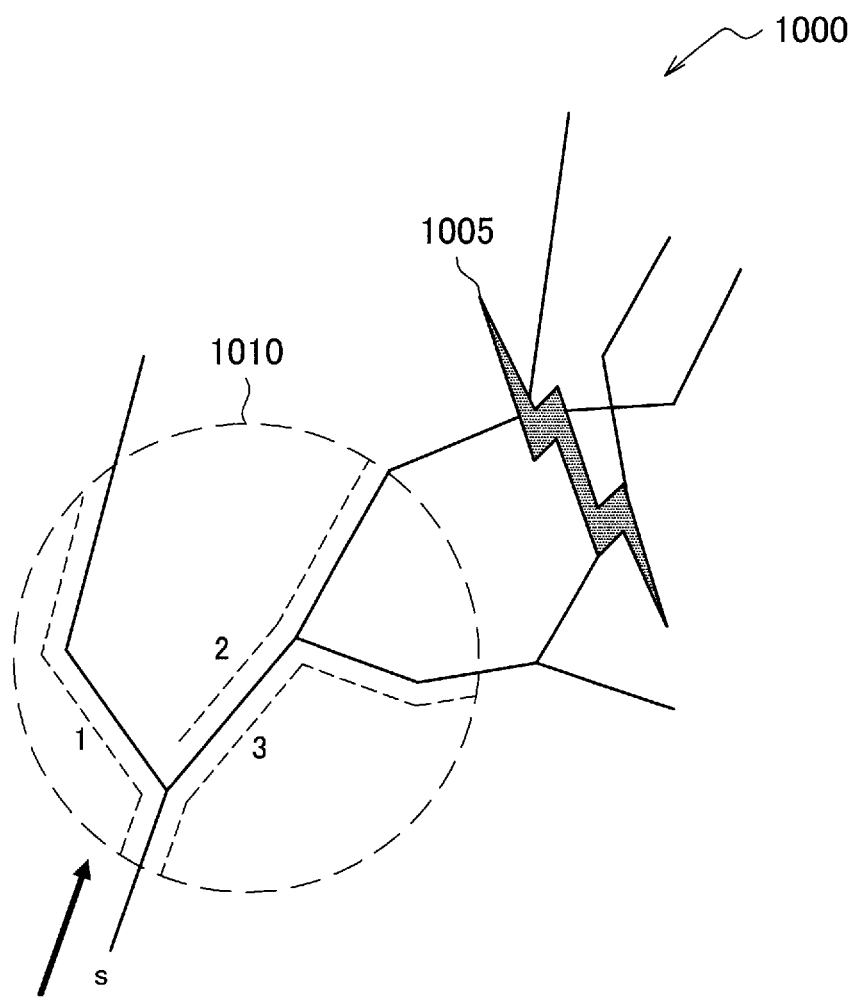

FIG. 10 shows further embodiments of the disclosure. In FIG. 10, the vasculature shown in FIG. 8 is redrawn. However, in this embodiment, the vasculature 1000 has a cut 1005 across several branches. During endoscopic procedures, information pertaining to the physiological status of the patient may not be apparent from the image, such as the heart or breathing rate, or blood flow anomalies. These may indicate nearby cuts/constrictions located outside the field of view of the image. Failing to identify changes in physiological status may lead to complications and sub-optimal patient outcomes. The latter application is particularly relevant to procedures such as a surgical operation.

In order to identify the direction of the cut in FIG. 10, which is downstream of the imaged surface 1010, the blood pressure in the vessels is used to indicate the loss of pressure due to a cut. This is measured relatively by comparing the velocity and amplitude of the pulse wave within different vessel paths. The pulse wave being identified by the embodiments described above in respect of Eulerian processing.

The flow direction in the vessel with the lowest estimated pressure is used to estimate the direction of the cut that has occurred outside the field of view 1010 of the endoscope. This information is then relayed to the user by annotating the endoscope image with a directional indicator of the cut.

It is also possible that the blood pressure before the cut is made is observed. In this instance, the change is monitored and when the blood pressure drops by a predetermined amount over a predetermined period, a cut in the branch may be inferred.

As noted above, it is possible to determine a cut using a drop in blood pressure. However, it is also possible to detect a cut, blood congestion or other bleed point inside or outside of the imaging area using the landmarking technique. Specifically, as noted above, the use of patterns is described to determine a landmark. In the context of detecting a cut outside the imaging area, the pattern may be a pattern of blood flow, a cut or cuts or blood congestion.

Where the pattern is a blood flow, a cut or cuts or blood congestion, it is possible to determine the origin of the pattern (i.e. the location of the cut). In order to achieve this, for any given cut or point of blood congestion, the pattern is identified. This will be achieved in the same manner as described above in respect of the landmarking. Once the pattern has been identified as a cut or blood congestion, the location of the cut or blood congestion is noted and shown to the user.

As an alternative mechanism or an additional mechanism to determine the blood flow, cut or blood congestion, the pattern at the location is stored. Then, when the endoscope views the pattern again, a difference is determined between the first time the pattern is viewed and the second time the pattern is viewed. This difference is attributed to the change associated with the cut or cuts or point of blood congestion. This difference can identify certain characteristics associated with the cut or point of blood congestion. For example, the amount (volume) of blood may be reduced, the strength of the blood flow may have reduced or the like. This may give an indication of the success of any remedial action taken by the surgeon (for example, cauterising the cut) or an indication of the situation becoming worse and thus the need for remedial action. It is envisaged that if the strength of blood flow increases, the endoscope system may indicate to the surgeon to perform certain remedial actions.

Although the above describes identifying a pattern by comparing the stored pattern to the endoscope view, the endoscopy system may be configured to identify a pattern using object recognition. In object recognition, features of an object are used to identify an object rather than relying on seeing the entire object and matching the entire object to a stored representation of that object. Object recognition is known and so will not be described for brevity.

Of course, it is possible to identify a cut or blood congestion within the field of view of the endoscope where certain characteristic features of a cut or blood congestion are within the field of view. For example, a cut typically has an image characteristic which is a thin linear region of red blood. Therefore, the object recognition algorithm identifies a region meeting these characteristics and thus identifies a cut using these characteristic traits rather than having a cut exactly matching previous stored examples of cuts.

In order to identify a cut or cuts or blood congestion that is outside the field of view of the endoscope, it is possible to identify features within the field of view that is indicative of a cut located outside the field of view. For example, the tissue at a location below a cut is likely to be less red than surrounding tissue. This is because less blood is being fed to that tissue due to the cut. It is also possible to identify the severity of the cut in dependence upon the colour of the tissue. For example, where there is a severe cut, the tissue will look less red compared to the situation where the cut is less severe. Accordingly, it is possible to identify the location and severity of a cut depending on the colour or other image characteristic of a captured image even if the cut itself is not in the field of view of the camera.

In addition to using object recognition to detect a bleed point, object recognition may also be used to identify a landmark described above. This has the advantage of the endoscope system learning features of a landmark rather than comparing the captured landmark to stored landmarks so that the landmark may be changed more easily.

Figure 11:
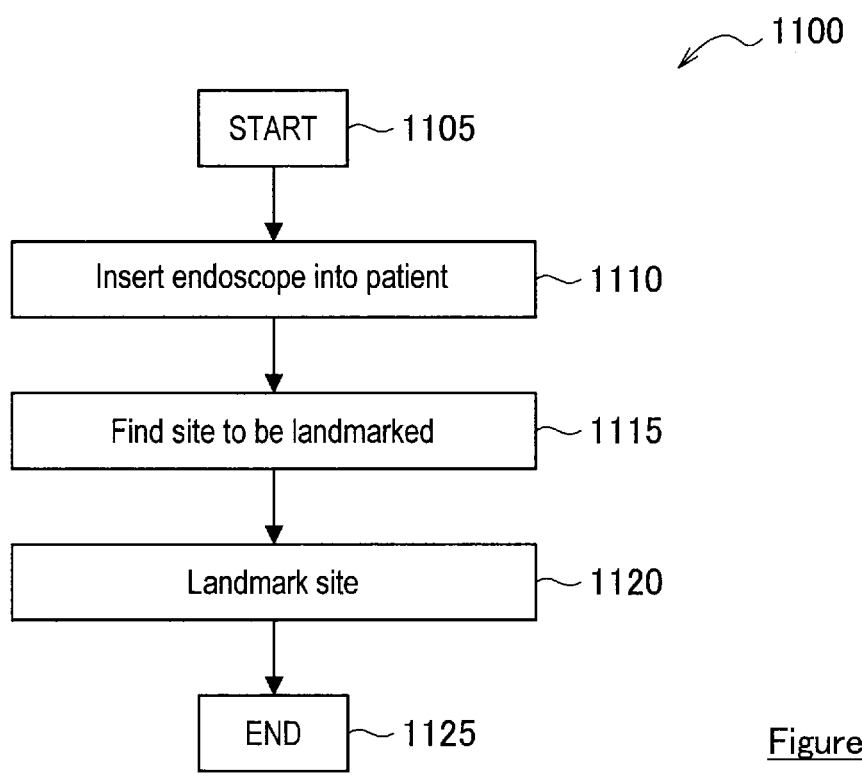
FIG. 11 shows a flow diagram according to embodiments according to the disclosure.

FIG. 11 shows a flow chart 1100 describing landmarking a site identified during endoscopy. The process starts at step 1105. The process moves to step 1110 where an endoscope is inserted into the patient. The surgeon moves the endoscope to identify an appropriate site to act as a landmark in step 1115. The surgeon performs landmarking by interacting with a user interface. In particular, when the surgeon identifies a site to landmark, the surgeon will interact with a User Interface to landmark the site. When landmarking the site, the CCU 5039 will, in embodiments, extract a pattern from the image identifying the landmark. This pattern may include, but not be limited to, the vasculature branch system, or the relative positions of the branches in the vasculature or some other pattern and to store this for later comparison. In other embodiments, of course, the pattern may be captured image itself. The process ends at step 1125.

Figure 12:
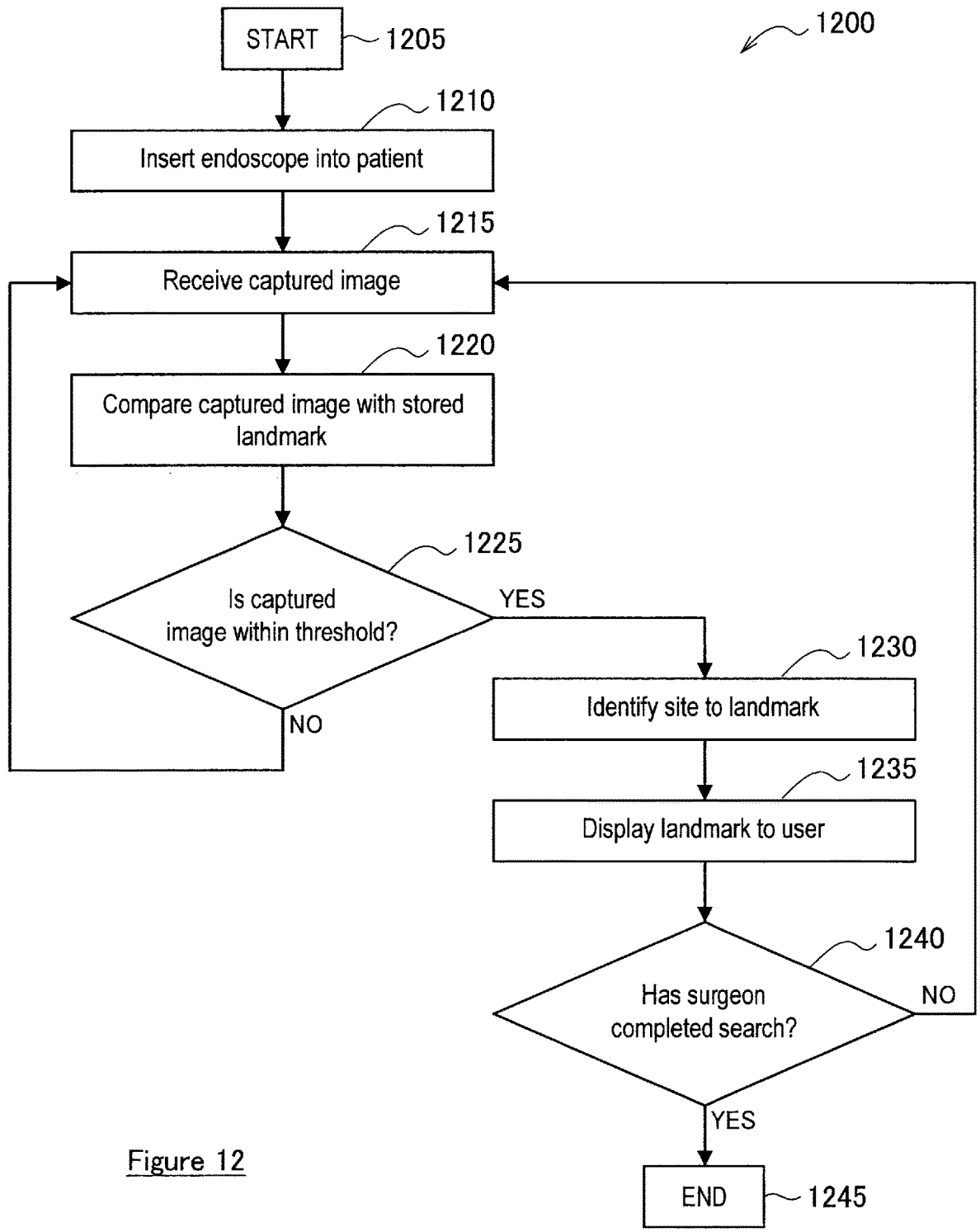
FIG. 12 shows a flow diagram according to embodiments according to the disclosure.

FIG. 12 shows a process 1200 showing the identification of a landmarked site. The process starts at step 1205. The endoscope is inserted into the patient at step 1210. The image from the endoscope is captured in step 1215. The captured image is compared with the stored landmark in step 1220. In embodiments, the relevant pattern (such as the vasculature) is extracted from the captured image and compared with the stored pattern. Of course, if the stored pattern is an image of the landmarked site, then the captured image is compared with the stored image of the landmarked site.

The process moves to step 1225, where the degree of similarity between the stored landmark and the captured image is determined. This degree is determined by determining whether the likeness of the captured image to the stored images is within a threshold value. The likeness value may be obtained from a multipoint closeness of fit algorithm.

In the event that the captured image is not similar to a stored pattern, then the no path is followed back to step 1215. Alternatively, if the captured image is similar, the yes path is followed and the process moves to step 1230. In step 1230, the image is identified as being a landmark site. The landmark is then displayed to the surgeon in step 1235. This would be displayed as an overlaid graphic on the image of the endoscope.

The process moves to step 1240 where it is determined whether the surgeon has completed the search for landmarks. To determine this, the surgeon will indicate using a Graphical User Interface whether he or she has completed the search. In the event that the surgeon has not completed the search, the "no" path is followed back to step 1215. In the event that the surgeon has completed his or her search, the process ends at step 1245 after following the "yes" path.

Various embodiments of the present disclosure are defined by the following numbered clauses:

1. A surgical imaging system comprising circuitry configured to accentuate an image characteristic of an area in captured images; identify the change of the image characteristic in the area; and identify the position of a physiological feature relative to the surgical device on the basis of the change in the image characteristic.

2. A surgical imaging system according to clause 1, wherein the circuitry is configured to accentuate the motion by decomposing each image into spatial frequency bands; applying the same temporal filter to each spatial frequency band and to amplify the filtered spatial frequency band by a predetermined amount.

3. A surgical imaging system according to clause 2, wherein the circuitry is configured to accentuate the motion by performing Eulerian video processing on the captured images.

4. A surgical imaging system according to any preceding clause, wherein the accentuation is on the basis of the colour change of the area in the image.

5. A surgical imaging system according to clause 4, wherein the colour change is a pulse wave across the surface of the object and the circuitry is configured to determine the distance to the internal organ by measuring the time difference between the change in colour in the area and the corresponding pulse wave across the surface of the object 6. A surgical imaging system according to any preceding clause, wherein the accentuation is on the basis of the motion of an object within the image.

7. A surgical imaging system according to clause 6, wherein the motion of the object is a pulse wave across the surface of the object.

8. A surgical imaging system according to any preceding clause, further comprising connector circuitry configured to be connected to a display, wherein the circuitry is configured to overlay an indication of the position of the internal organ onto one of the captured images to form a composite image and to provide the composite image to the connector circuitry.

9. A surgical imaging system according to any preceding clause, wherein the physiological feature is an internal organ or a bleed point.

10. A surgical imaging system comprising circuitry configured to: accentuate the colour and/or motion of an area in captured images; compare the accentuated motion to a stored accentuated motion and identify the material of the object based upon the comparison.

11. A surgical imaging system comprising circuitry configured to: accentuate the colour and/or motion of an area in captured images; compare the accentuated motion to a stored accentuated motion and identify a landmark based on the comparison.

12. A surgical imaging system according to clause 11, wherein the circuitry is configured to identify vasculature as the landmark.

13. A surgical imaging system according to clause 11, wherein the circuitry is configured to identify a bleed point as the landmark.

14. A surgical imaging system comprising circuitry configured to: accentuate the colour and/or motion of an area in captured images; and identify a landmark based on a characteristic feature in the accentuated motion.

15. A surgical imaging system according to clause 14, wherein the circuitry is configured to identify a bleed point as the landmark.

16. A surgical imaging system comprising circuitry configured to: identify a captured image of a pattern of vasculature as a landmark; store the captured pattern; compare subsequent captured images to the stored pattern and identify the subsequent image as the landmark on the basis of the comparison.

17. A surgical imaging system according to clause 1, 10, 11, 14 or 16, comprising image sensor circuitry configured to capture the plurality of images.

18. A surgical imaging method comprising: accentuating an image characteristic of an area in captured images; identifying the change of the image characteristic in the area; and identifying the position of a physiological feature relative to a surgical device on the basis of the change in the image characteristic.

19. A surgical imaging method according to clause 18, comprising: accentuating the motion by decomposing each image into spatial frequency bands; applying the same temporal filter to each spatial frequency band and amplifying the filtered spatial frequency band by a predetermined amount.

20. A surgical imaging method according to clause 19, comprising accentuating the motion by performing Eulerian video processing on the captured images.

21. A surgical imaging method according to any one of clause 18 to 20, wherein the accentuation is on the basis of the colour change of the area in the image.

22. A surgical imaging method according to clause 21, wherein the colour change is a pulse wave across the surface of the object and the circuitry is configured to determine the distance to the internal organ by measuring the time difference between the change in colour in the area and the corresponding pulse wave across the surface of the object 23. A surgical imaging method according to any one of clause 18 to 22, wherein the accentuation is on the basis of the motion of an object within the image.

24. A surgical imaging method according to clause 23, wherein the motion of the object is a pulse wave across the surface of the object.

25. A surgical imaging method according to any one of clause 18 to 24, further comprising overlaying, on a display, an indication of the position of the internal organ onto one of the captured images to form a composite image and to provide the composite image to the connector circuitry.

26. A surgical imaging method according to any one of clause 18 to 25, wherein the physiological feature is an internal organ or a bleed point.

27. A surgical imaging method comprising: accentuating the colour and/or motion of an area in the captured images; comparing the accentuated motion to a stored accentuated motion and identifying the material of the object based upon the comparison.

28. A surgical imaging method comprising: accentuating the colour and/or motion of an area in the captured images; comparing the accentuated motion to a stored accentuated motion and identifying a landmark based on the comparison.

29. A surgical imaging method according to clause 28, wherein the landmark is vasculature.

30. A surgical imaging method according to clause 28, wherein the landmark is a bleed point.

31. A surgical imaging method comprising: accentuating the colour and/or motion of an area in the captured images; and identifying a landmark based on a characteristic feature in the accentuated motion.

32. A surgical imaging method according to clause 31, wherein the landmark is a bleed point.

33. A surgical imaging method comprising: identifying a captured image of a pattern of vasculature as a landmark; storing the captured pattern; comparing subsequent images captured by the image sensor to the stored pattern and identifying the subsequent image as the landmark on the basis of the comparison.

34. A computer program product comprising computer readable instructions which, when loaded onto a computer, configure the computer to perform a method according to any one of clause 18 to 33.

Obviously, numerous modifications and variations of the present disclosure are possible in light of the above teachings. It is therefore to be understood that within the scope of the appended claims, the disclosure may be practiced otherwise than as specifically described herein.

In so far as embodiments of the disclosure have been described as being implemented, at least in part, by software-controlled data processing apparatus, it will be appreciated that a non-transitory machine-readable medium carrying such software, such as an optical disk, a magnetic disk, semiconductor memory or the like, is also considered to represent an embodiment of the present disclosure.

It will be appreciated that the above description for clarity has described embodiments with reference to different functional units, circuitry and/or processors. However, it will be apparent that any suitable distribution of functionality between different functional units, circuitry and/or processors may be used without detracting from the embodiments.

Described embodiments may be implemented in any suitable form including hardware, software, firmware or any combination of these. Described embodiments may optionally be implemented at least partly as computer software running on one or more data processors and/or digital signal processors. The elements and components of any embodiment may be physically, functionally and logically implemented in any suitable way. Indeed the functionality may be implemented in a single unit, in a plurality of units or as part of other functional units. As such, the disclosed embodiments may be implemented in a single unit or may be physically and functionally distributed between different units, circuitry and/or processors.

Although the present disclosure has been described in connection with some embodiments, it is not intended to be limited to the specific form set forth herein. Additionally, although a feature may appear to be described in connection with particular embodiments, one skilled in the art would recognize that various features of the described embodiments may be combined in any manner suitable to implement the technique.

Brief Description of Eulerian Video Processing

In summary, oscillations in the pixel intensity values (RGB) in an image at a specific position which occur within a frequency range are amplified. In principle, we take the 3D cube of video data (X, Y, T) and apply a band pass frequency filtering operation only in the T direction.

1. The processing is performed independently at each specific spatial location. Therefore, it is desirable (although not essential) that the image is reasonably stationary over the temporal frequency amplification window. This can be improved by applying video stabilisation algorithms if necessary.

2. Since the image signal is amplified there will be issues with amplifying noise in the image. In order to mitigate this, some form of spatial averaging is required, to ensure that the signal to noise ratio is sufficiently high for a real signal (operating over some spatial extent) to be amplified. This can be done in many different ways, for example:

a. The image can be smoothed and down sampled prior to the operation, but this results in a smaller, lower resolution final image/video b. The image can be separated into different spatial frequency bands, e.g. with a Laplacian pyramid. Here the image is smoothed with a selected small spatial smoothing convolution e.g. a spatial Gaussian (matched to the down sampling rate), and subtracted from the previous (unsmoothed) image, then down sampled e.g. to half size. This operation is repeated until a small residual image remains. The temporal frequency amplification is then performed for each spatial bandpass image (and the residual image) separately, with an amplification factor depending on the expected signal to noise ratio for that band (which should improve for larger spatial frequencies and therefore the amplification factor can be higher). The band pass amplified images are then recombined (by up sampling and adding in) into the final complete image/video.

3. Temporal amplification is performed along each single pixel time sequence data separately by applying a band-pass filter to that data for example using the Discrete Cosine Transform (DCT), where a window of data is transformed into the frequency domain, point multiplied by the DCT of the filter and then transformed back into the pixel data domain, for example selecting and amplifying frequencies between 0.5 and 5 Hz. The band pass filter might be dynamic—e.g. tracking the heart rate (supplied by an Electrocardiogram (ECG) signal or pulse oximeter) or fixed and may be narrow band or broad band. The amplification values may be fixed, calculated from some measure of signal to noise ratio or adjusted by the user.

4. The amplification of oscillatory motion signals is only applicable to small spatial oscillations and low levels of amplification, otherwise significant distortions occur 5. Temporal band pass filters used for amplification can be chosen from a wide range of options—ideal (square pulse) filters, second order Infinite impulse response (IIR) filters etc, depending on the application. Filters can be generated for user supplied cutoff frequencies and then applied, e.g. in real-time.

6. Since the processing operates over a pixel time series, there will be some inherent latency in any real-time implementation related to the time window used for temporal amplification It is possible that Eulerian algorithms may give better performance for visualising larger oscillatory motions and which is less noise sensitive. This is achieved by the spatial decomposition being performed by a processing pyramid which decomposes in both scale and direction (using quadrature filters), and temporal amplification is performed on the phase of this pyramid [1].

Training Phase for Intervening Objects and Tissue Samples

In order to determine the effect on the heart and lung oscillations of intervening objects such as the air filed stomach or indeed various types of tissues, a training phase must be carried out. During the training phase, the refraction, reflection and attenuation patterns caused by these objects are captured at various points in the patient. It is anticipated that the training will occur once and the results collated and stored within the storage medium in the endoscope system during manufacture.

During the training phase, the location of the endoscope is continually monitored using magnetic imaging. In order to obtain representative values for the refraction, reflection and attenuation patterns, the heart and lung function of the patient during the training phase must be representative of patients who will be subjected to endoscopy. This will include a patient having an average heart beat with average heart strength, average lung function and an average body fat composition (as excesses of body fat may produce erroneous training results). Of course, other patients lying outside the norm may be selected to obtain outlying values. In this case, a correlation may exist between the refraction, reflection and attenuation patterns at the position of the endoscope and the position of the patient relative to the average and the outlier under test. In other words, if the body fat of the patient was exactly between the average and the outlier, the attenuation of the wave front may also be exactly between that expected for the average and the outlier at the same position in the patient's body.

Similarly, the effect of various different materials may be captured during the training phase. For example, with the patients selected during the training phase, one may have a malignant tumour and the other may have a benign tumour at similar locations. The refraction, reflection and attenuation patterns caused by the malignant tumour and the benign tumour at a given set of known locations may be observed and recorded. These may be stored in the endoscopic system during manufacture and used when operating the system to identify the likelihood of the tumour being malignant or benign.

The invention claimed is:

1. A surgical imaging system comprising circuitry configured to
   accentuate an image characteristic of an area in captured images having a field of view;
   identify a change of the image characteristic in the area; and
   identify a position of a physiological feature relative to a surgical device outside of a field of view based on the change in the image characteristic.

2. A surgical imaging system according to claim 1, wherein the circuitry is configured to accentuate the change by
   decomposing each image into spatial frequency bands;
   applying the same temporal filter to each spatial frequency band; and
   amplifying to amplify the filtered spatial frequency band by a predetermined amount.

3. A surgical imaging system according to claim 2, wherein the circuitry is configured to accentuate the change by performing Eulerian video processing on the captured images.

4. A surgical imaging system according to claim 1, wherein the accentuation is based on a color change of the area in the image.

5. A surgical imaging system according to claim 4, wherein the color change is a pulse wave across a surface of the physiological feature and the circuitry is configured to determine a distance to the physiological feature by measuring a time difference between the change in color in the area and a corresponding pulse wave across the surface of the physiological feature.

6. A surgical imaging system according to claim 1, wherein the accentuation is based on motion of the physiological feature within the image.

7. A surgical imaging system according to claim 6, wherein the motion of the physiological feature is a pulse wave across a surface of the physiological feature.

8. A surgical imaging system according to claim 1, further comprising connector circuitry configured to be connected to a display, wherein the circuitry is configured to overlay an indication of the position of the physiological feature onto one of the captured images to form a composite image and to provide the composite image to the connector circuitry.

9. A surgical imaging system according to claim 1, wherein the physiological feature is an internal organ or a bleed point.

10. A surgical imaging system according to claim 1, wherein the circuitry is further configured to:
measure a location of the surgical device using an external imager;
measure an image characteristic associated with the physiological feature when the surgical device is inserted;
move the surgical device and repeat measurements;
store measured image characteristics and positions; and
identify the position of the physiological feature relative to the surgical device based on the change in the image characteristic includes comparing changes in image characteristics to stored image characteristics.

11. A surgical imaging method comprising:
accentuating an image characteristic of an area in captured images having a field of view;
identifying a change of the image characteristic in the area; and
identifying a position of a physiological feature relative to a surgical device outside of the field of view based on the change in the image characteristic.

12. A surgical imaging method according to claim 11, comprising: accentuating the change by decomposing each image into spatial frequency bands; applying the same temporal filter to each spatial frequency band and amplifying the filtered spatial frequency band by a predetermined amount.

13. A surgical imaging method according to claim 12, comprising accentuating the change by performing Eulerian video processing on the captured images.

14. A surgical imaging method according to claim 11, wherein the accentuation is based on a color change of the area in the image.

15. A surgical imaging method according to claim 14, wherein the color change is a pulse wave across a surface of the physiological feature and the circuitry is configured to determine a distance to the physiological feature by measuring a time difference between the change in color in the area and a corresponding pulse wave across a surface of the physiological feature.

16. A surgical imaging method according to claim 11, wherein the accentuation is based on motion of the physiological feature within the image.

17. A surgical imaging method according to claim 16, wherein the motion of the physiological feature is a pulse wave across a surface of the physiological feature.

18. A surgical imaging method according to claim 11, further comprising overlaying, on a display, an indication of the position of the physiological feature onto one of the captured images to form a composite image and to provide the composite image to the display.

19. A surgical imaging method according to claim 11, wherein the physiological feature is an internal organ or a bleed point.

20. A non-transitory computer readable storage device having computer readable instructions which, when loaded onto a computer, configure the computer to perform a method according to claim 11.

21. A surgical imaging method according to claim 11, further comprising:
measuring a location of the surgical device using an external imager;
measuring an image characteristic associated with the physiological feature when the surgical device is inserted;
moving the surgical device and repeat measurings;
storing measured image characteristics and positions; and
identifying the position of the physiological feature relative to the surgical device based on the change in the image characteristic includes comparing changes in image characteristics to stored image characteristics.

* * * * *